United States Patent [19]

Hou et al.

[11] 4,250,259
[45] Feb. 10, 1981

[54] MICROBIOLOGICAL PRODUCTION OF KETONES FROM $C_3$-$C_6$ SECONDARY ALCOHOLS

[75] Inventors: Ching-Tsang Hou; Ramesh N. Patel, both of Edison, N.J.; Allen I. Laskin, New York, N.Y.

[73] Assignee: Exxon Research & Engineering Co., Florham Park, N.J.

[21] Appl. No.: 25,727

[22] Filed: Mar. 30, 1979

Related U.S. Application Data

[63] Continuation-in-part of Ser. No. 896,475, Apr. 14, 1978, abandoned, and Ser. No. 896,476, Apr. 14, 1978, abandoned.

[51] Int. Cl.³ .......................... C12P 7/26; C12P 7/04; C12N 1/30; C12N 9/02
[52] U.S. Cl. .................................. 435/148; 435/150; 435/157; 435/160; 435/189; 435/190; 435/250; 435/253; 435/822; 435/858
[58] Field of Search ............... 435/148, 220, 183, 189, 435/250, 190, 253, 160, 822, 858, 150, 157

[56] References Cited

U.S. PATENT DOCUMENTS

| | | | |
|---|---|---|---|
| 3,326,771 | 6/1967 | Leavitt | 435/183 X |
| 3,344,037 | 9/1967 | Leavitt | 435/190 X |
| 3,930,947 | 1/1976 | Morinaea et al. | 435/822 X |

OTHER PUBLICATIONS

Patel et al., Microbial Oxidation of Methane & Methanol:Crystallization & Properties of Methanol Dehydrogenase from Methylosinus Sporium J. Bact., vol. 128, No. 1 (1976), pp. 413–424.

Thomson et al., "Acetone Production by Methylobacteria" Chemical Abstracts (1976) Abstract No. 156225t.

*Primary Examiner*—R. B. Penland
*Attorney, Agent, or Firm*—Albert P. Halluin

[57] ABSTRACT

A process is disclosed for the microbiological production of ketones from $C_3$-$C_6$ secondary alcohols by contacting $C_3$-$C_6$ secondary alcohols under aerobic conditions with resting microbial cells derived from a microorganism of enzyme preparation derived from said cells, wherein the microorganism has been previously grown under aerobic conditions in a nutrient medium containing a methyl-radical donating compound. Typical methyl-radical donating compounds are: methane, methanol, dimethyl ether, methylamine, methyl formate, methyl carbonate, ethanol, propanol, butanol, etc. Isolation and purification of a novel $C_3$-$C_6$ secondary alcohol dehydrogenase enzyme is also disclosed.

29 Claims, No Drawings

MICROBIOLOGICAL PRODUCTION OF KETONES FROM $C_3$-$C_6$ SECONDARY ALCOHOLS

CROSS-REFERENCE TO RELATED APPLICATIONS

This application is a continuation-in-part of U.S. Application Ser. Nos. 896,475 and 896,476 filed Apr. 14, 1978 both abandoned. This application is related to U.S. Application Ser. No. 24,302 filed on Mar. 27, 1979 entitled, "Secondary Alcohol Dehydrogenase Enzyme and Use Thereof."

FIELD OF THE INVENTION

The present invention relates to the conversion of $C_3$-$C_6$ alkanes or secondary alcohols to methyl ketones, i.e., acetone or 2-butanone. More particularly, it relates to the formation of $C_3$-$C_6$ methyl ketones from $C_3$-$C_6$ alkanes or $C_3$-$C_6$ secondary alcohols, through the action of oxygen and microbial cells of induced methylotrophic microorganisms or enzyme preparations derived therefrom.

BACKGROUND OF THE INVENTION

Methane is one of the most expensive carbon sources for microbial growth. It is known that there are many microorganisms capable of growing on a culture medium in the presence of methane as the principle carbon source. However, not all of these microorganisms share good growth characteristics. It is also known that methane-grown microorganisms can be used to convert methane to methanol under aerobic conditions.

These methane-utilizing microorganisms are generally known as "methylotrophs". The classification system for methylotrophs proposed by R. Whittenbury et al. (*J. of Gen. Microbiology*, 61, 205-218 (1970)) is the most widely recognized. In their system, the morphological characteristics of methane-oxidizing bacteria are divided into five groups: Methylosinus, Methylocystis, Methylomonas, Methylobacter and Methylococcus.

Recently, Patt, Cole and Hanson (*International J. Systematic Bacteriology*, 26, (2) 226-229 (1976)) disclosed that methylotrophic bacteria are those bacteria that can grow non-autotrophically using carbon compounds containing one or more carbon atoms but containing no carbon-carbon bonds. Patt et al. have proposed that methylotrophs should be considered "obligate" if they are capable of utilizing only carbon compounds containing no carbon-carbon bonds (e.g., methane, methanol, dimethylether, methylamines, etc.) as the sole sources of carbon and energy whereas "facultative" methylotrophs are those organisms that can use both compounds containing no carbon-carbon bonds as well as compounds having carbon-carbon bonds as the sources of carbon and energy. In their paper, Patt et al. disclosed a methane-oxidizing bacterium, which they identified as *Methylobacterium organophilum* sp nov. (ATCC 27,886). This bacterium presumably differs from all previously described genera and species of methane-oxidizing bacteria because of its ability to utilize a variety of organic substrates with carbon-carbon bonds as sources of carbon and energy.

It is now well recognized that there are two types of methylotrophic microorganisms based on their ability to grow on carbon-containing substrates. One type has been referred to as "methane-utilizers" and the other has been referred to as "methanol-utilizers". The methanol-utilizers are unable to grow in the presence of methane as the sole carbon and energy source, but will grow in the presence of methanol, methylamine, etc. The methane-utilizers are capable of growing on a plurality of $C_1$-type compounds, including methane, methanol, dimethyl ether, etc. Within the group of methane-utilizing methylotrophs and methanol-utilizing methylotrophs, there are obligate and facultative types of methylotrophic microorganisms. The obligate methane-utilizer type methylotrophic microorganisms will only grow on $C_1$-type compounds, e.g., methane, methanol, dimethyl ether, methyl formate, methyl carbonate, etc. The facultative methane-utilizer type methylotrophic microorganisms will not only grow on the above-mentioned $C_1$-type compounds, but will also grow on other organic compounds such as glucose. The obligate methanol-utilizer type methylotrophic microorganisms will grow on $C_1$ compounds, e.g., methanol, methylamine, but not on methane or on organic compounds such as glucose. The facultative methanol-utilizer type methylotrophic microorganisms will grow on the $C_1$-type compounds mentioned above (but not methane) and various other organic compounds such as glucose.

DESCRIPTION OF THE PRIOR ART

Leadbetter and Foster, (*Arch. Microbiology*, 30, 81-118 (1959) "Studies on Some Methane-Utilizing Bacteria") reported that microbial cells derived from *Pseudomonas methanica* (presently named *Methylomonas methanica*) oxidizes n-propane and n-butane to the corresponding alcohols, ketones and carboxylic acids when present simultaneously in growth cultures containing methane as the growth substrate. Leadbetter et al. state on page 103: "Propane or n-butane were not oxidized by washed cells. However, they were oxidized when present simultaneously in growth cultures with methane as the growth substrate". On page 102, Leadbetter et al. speculate that the secondary alcohol is an intermediate product in the conversion of propane to acetone.

The type of process described by Leadbetter et al. has been referred to as a "co-oxidation technique" since nongrowth hydrocarbons are oxidized when present as cosubstrates in a medium in which one or more different hydrocarbons are furnished for growth. As discussed above, Leadbetter et al. employed this technique wherein *Pseudmonas methanica* was grown at the expense of methane and a series of homologous oxidation products were obtained from the cosubstrate gases, e.g., from ethane were produced ethanol, acetaldehyde, and acetic acid; from propane were produced n-propanol, propionic acid, and acetone; from n-butane were produced n-butanol, n-butyric acid, and 2-butanone.

Several published papers have referred to the Leadbetter et al. paper in reference to the production of ketones from alkanes in various attempts to understand the mechanism of this conversion (i.e., does the conversion proceed through a secondary alcohol intermediate?).

These prior art workers did not describe a process wherein "resting" microbial cells or their enzyme preparations derived from methylotrophic microorganisms aerobically grown on $C_1$-type compounds (e.g., methane, methanol, methylamine, etc.) will convert $C_3$-$C_6$ alkanes or $C_3$-$C_6$ secondary alcohols to the corresponding methyl ketones. As it is well known "resting" microbial cells are distinguishable from "growing" microbial cells in that the former are not maintained in a growth medium, i.e., containing a carbon and nitrogen source, whereas the latter are maintained in a growth medium where they can actively grow and multiply.

While A. W. Thompson, J. G. O'Neill and J. F. Wilkinson (*Arch. Microbiol.*, 109, 243–246 (1976) "Acetone Production by Methylobacteria") have disclosed that acetone was observed during the metabolism of ethane and products of ethane oxidation by washed suspensions of methylotrophic microorganisms such as *Methylosinus trichosporium* OB3b and *Methylomonas albus* BG8, Thompson et al. do not disclose the production of ketones from $C_3$-$C_6$ alkanes or $C_3$-$C_6$ secondary alcohols.

Hutchinson, Whittenbury and Dalton (*J. Theor. Biol.*, 58, 325–335 (1976) "A Possible Role of Free Radicals in the Oxidation of Methane by *Methylococcus capsulatus*") and Colby and Dalton (*J. Biochem.*, 157, 495–497 (1976) "Some Properties of a Soluble Methane Mono-Oxygenase From *Methylococcus capsulatus* Strain Bath") reported that ethylene is oxidized by the soluble methane mono-oxygenase from *Methylococcus capsulatus* Strain Bath. The latter investigators reported that the "particulate membrane preparations" of *Methylococcus capsulatus* Strain Bath did not have methane-oxygenase activity as determined by the bromomethane disappearance test.

Cerniglia, Blevins and Perry, (*Applied and Environmental Microbiology*, 32, (6) 764–768 (1976) "Microbial Oxidation and Assimilation of Propylene") described the oxidation of propylene by microorganisms to the corresponding alcohols and carboxylic acids.

Most recently, Colby, Stirling and Dalton, (*J. Biochem.*, 165, 395–402 (August, 1977)) "The Soluble Methane Mono-Oxygenase of *Methylococcus capsulatus* (Bath) Its Ability to Oxygenate n-Alkanes, n-Alkenes, Ethers, and Alicyclic Aromatic and Heterocyclic Compounds") disclosed that the soluble fraction of *Methylococcus capsulatus* Strain Bath is a very non-specific oxygenase in that it oxidizes alkanes to alcohols, alkenes to 1,2-epoxides, dimethylether to ethanol and ethanal, styrene to styrene epoxide and pyridine to pyridine N-oxide.

On the basis of $^{18}O_2$ incorporation from $^{18}O_2$ into the cellular constituents of *Pseudomonas methanica* Leadbetter and Foster (*Nature*, 184: 1428–1429 (1959) "Incorporation of Molecular Oxygen in Bacterial Cells Utilizing Hydrocarbons For Growth") suggested that the initial oxidative attack on methane involves an oxygenase. Higgins and Quayle (*J. Biochem.*, 118: 201–208 (1970) "Oxygenation of Methane by Methane-Grown *Pseudomonas methanica* and *Methanomonas methanooxidans*") isolated $CH_3^{18}OH$ as the product of methane oxidation when suspensions of *Pseudomonas methanica* or *Methanomonas methanooxidans* were allowed to oxidize methane in $^{18}O_2$-enriched atmospheres. The subsequent observation of methane-stimulated NADH oxidation catalyzed by extracts of *Methylococcus capsulatus* by Ribbons (*J. Bacteriol.*, 122: 1351–1363 (1975) "Oxidation of $C_1$-Compounds by Particulate Fractions From *Methylococcus capsulatus*: Distribution and Properties of Methane-Dependent Reduced Nicotinamide Adenine Dinucleotide Oxidase (methane hydroxylase)") and Ribbons and Michalover, FEBS Lett. 11: 41–44 (1970) "Methane Oxidation by Cell-Free Extracts of *Methylococcus capsulatus*" or *Methylomonas Methanica Ferenci* (FEBS Lett. 41: 94–98 (1974) "Carbon Monoxide-Stimulated Respiration in Methane-Utilizing Bacteria") suggested that the enzyme responsible for this oxygenation in a monooxygenase. These workers relied on indirect enzyme assays, measuring methane-stimulated NADH disappearance spectrophotometrically or methane-stimulated $O_2$ disappearance polarographically. Recently, methane monooxygenase systems were partially purified from *Methylosinus trichosporium* OB3b (Tonge, Harrison and Higgins, *J. Biochem.*, 161: 333–344 (1977) "Purification and Properties of the Methane Monooxygenase Enzyme System From *Methylosinus trichosporium* OB3b"); and Tonge, Harrison, Knowles and Higgins, FEBS Lett., 58: 293–299 (1975) "Properties and Partial Purification of the Methane-Oxidizing Enzyme System From *Methylosinus trichosporium*") and *Methylococcus capsulatus* (Bath) (Colby and Dalton, *J. Biochem.*, 171: 461–468 (1978) "Resolution of the Methane Mono-Oxygenase of *Methylococcus capsulatus* (Bath) Into Three Components" and Colby, Stirling and Dalton, *J. Biochem.*, 165: 395–402 (1977) "The Soluble Methane Mono-Oxygenase of *Methylococcus capsulatus* (Bath), "Its Ability to Oxygenate n-Alkanes, n-Alkenes, Ethers, and Alicyclic, Aromatic and Heterocyclic Compounds").

The microbiological formation of methyl ketones in mammals, bacteria and fungi is well known. However, the ketone is formed by decarboxylation of a beta-keto acid and has, therefore, one less carbon atom than the precursor. On the other hand, bacterial formation of methyl ketones from n-alkanes, demonstrated first by Leadbetter and Foster (*Arch. Mikrobiol.*, 35: 92–104 (1960)) represents a unique alpha-oxidation, with no change in the carbon skeleton. However, in this letter report it was stated that the ketone formation was by co-oxidation in the presence of the growth substrate and indicated that no activity was found with the resting cells.

Phenazine methosulfate (PMS)-dependent methanol dehydrogenase has been extensively reported from many methylotrophic bacteria. This enzyme oxidizes primary alcohols from $C_1$ to $C_{10}$ but does not oxidize secondary alcohols. Nicotinamide ademine dinucleocide (NAD)-dependent alcohol dehydrogenases have been reported from liver and from yeast. These alcohol dehydrogenases oxidize primary alcohols and acetaldehyde, but have no activity on methanol. In addition, the alcohol dehydrogenases from yeast and liver also oxidize some secondary alcohols at a very low rate ($<1\%$ of their ethanol activity). NAD(P)-dependent alcohol dehydrogenases were also reported in Pseudomonas, *E. coli* and Leuconostoc. However, these enzymes were active only toward long-chain primary alcohols or hydroxy fatty acids. Recently, an NAD-linked methanol oxidizing enzyme was reported in a crude extract from yeast (Mehta, R. J., *J. Bacteriol.*, 124, 1165–1167 (1975). To our knowledge there is no report in the literature of a secondary alcohol-specific alcohol dehydrogenase (SADH) enzyme.

Since Ogata et al. (*J. Ferm. Technol.*, 48: 389–396 (1970)) first reported the assimilation of methanol by a yeast, many methanol-utilizing strains have been isolated from natural sources or found in stock culture collections. Interest in the cultivation of microorganisms on cheap and abundantly available compounds, such as methanol has increased greatly as a result of the potential importance of microbial protein as a food or fodder material. The production of single-cell protein (SCP) from methanol-grown yeasts have been discussed in several publications. Oxidation of methanol and other primary alcohols in yeasts has been shown to be catalyzed by an alcohol oxidase. Alcohol oxidase contained flavin adenine dinucleotide (FAD) as a prosthetic group. Secondary alcohols were not oxidized by this alcohol oxidase.

BRIEF DESCRIPTION OF THE PRESENT INVENTION

It has now been discovered that $C_3$-$C_6$ methyl ketones, e.g., acetone and 2-butanone can be prepared by a process comprising contacting a $C_3$-$C_6$ alkane or a $C_3$-$C_6$ secondary alcohol under aerobic conditions in a non-nutrient medium containing resting microbial cells derived from obligate or facultative methylotrophic microorganisms or enzyme preparations derived from said cells, wherein said microorganisms have been previously cultivated under aerobic conditions in a mineral nutrient medium containing an oxygenase and/or dehydrogenase enzyme inducer as the growth and energy source. Examples of such inducers include methane (in the case of methane-utilizing methylotrophic microorganisms) methanol, dimethyl ether, methylamine, methyl formate, methyl carbonate, ethanol, propanol, butanol, etc.

The microbial cells or the enzyme preparations derived from the cells to be used in converting the $C_3$-$C_6$ alkanes to the corresponding ketones may be derived from obligate or facultative methane-utilizing type methylotrophic microorganisms, but not the methanol-utilizing type methylotrophic microorganisms. The microbial cells or the enzyme preparations derived from the cells to be used in converting $C_3$-$C_6$ secondary alcohols to the corresponding ketones may be derived from either the obligate or facultative methane- or methanol-utilizing type methylotrophic microorganisms.

It has also been discovered that methylotrophic yeast strains may be aerobically grown on a plurality of methyl radical donating carbon-containing compounds, such as methanol, methylamine, methyl formate, methyl carbonate, dimethyl ether, etc., to produce microbial cells or enzyme preparations derived therefrom and are capable of aerobically converting $C_3$-$C_6$ linear secondary alcohols to the corresponding methyl ketones.

As an additional discovery we have identified a nicotinamide adenine dinucleotide (NAD*)-dependent secondary alcohol dehydrogenase in cell-free extracts of various hydrocarbon-utilizing microbes, including bacteria and yeast. This enzyme is also found in cells grown on methanol. It specifically and stoichiometrically oxidizes $C_3$-$C_6$ secondary alcohols to their corresponding methyl ketones. This enzyme; has been purified 2600 fold and shows a single protein band on acrylamide gel electrophoresis. It has a molecular weight of 95,000±3000 dalton. The bacterial SADH consists of two subunits of 48,000 dalton and two atoms of zinc per molecule of enzyme protein. It oxidizes secondary alcohols, notably 2-propanol and 2-butanol. Primary alcohols are not oxidized by SADH.

As discussed above, the obligate methane-utilizing methylotrophic microorganisms are capable of growing on methane, methanol and a plurality of methyl radical donating compounds, e.g., dimethyl ether, methyl formate, methyl carbonate, etc. The facultative methane-utilizing methylotrophic microorganisms not only grow on methane, methanol and various methyl radical donating compounds as mentioned above, but they are also capable of growing on various other organic compounds such as glucose.

The obligate methanol utilizing methylotrophic microorganisms are not capable of growing on methane, but are capable of growing on methanol and other methyl radical donating type compounds such as methylamine, methyl formate, methyl carbonate, etc. The facultative methanol-utilizing methylotrophic microorganisms, like the obligate methanol-utilizing methylotrophic microorganisms are not capable of growing on methane, but are capable of growing on methanol, the above-mentioned methyl-containing and other organic compounds such as $C_2$-$C_6$ alcohols and glucose. For the purpose of the present invention, however, the obligate or facultative methanol-utilizing microorganisms are to be grown on the alcohol dehydrogenase-inducing substrate, i.e., methanol, ethanol, propanol, butanol, methylamine and methyl formate, etc.

DETAILED DESCRIPTION OF THE PRESENT INVENTION

The term "microorganism" is used herein in its broadest sense to include not only bacteria, but also yeasts, filamentous fungi, actinomycetes and protozoa. Preferably, the microorganisms will include bacteria, and more preferably the bacteria capable of oxidizing methane and methyl-radical donating carbon-containing compounds.

The term "enzyme preparation" is used to refer to any composition of matter that exhibits the desired oxygenase or dehydrogenase enzymatic activity. The term is used to refer, for example, to live whole cells, dried cells, cell extracts and refined and concentrated preparations derived from the cells, especially purified secondary alcohol dehydrogenase and its NAD+ cofactor and metal requirement. Enzyme preparations may be either in dry or liquid form. The term also includes the immobilized form of the enzyme, e.g., the whole cells of the methane or methyl-radical-grown microorganisms or enzyme extracts immobilized or bound to an insoluble matrix by covalent chemical linkages, absorption and entrapment of the enzyme within a gel lattice having pores large enough to allow the molecules of the substrate and of the product to pass freely, but small enough to retain the enzyme. The term "enzyme preparation" also includes enzymes retained within hollow fiber membranes, e.g., as disclosed by Rony, *Biotechnology and Bioengineering* (1971).

The term "particulate fraction" refers to the enzyme activity in the precipitated or sedimented material when the supernatant after centrifuging broken cells at 10,000×g. for 30 minutes is centrifuged for 1 hour at 10,000×g. or greater.

The classification system of methane-oxidizing bacteria proposed by R. Whittenbury, K. C. Phillips and J. F. Wilkinson [*J. Gen. Microbiology*, 61, 205-218 (1970) (hereinafter Whittenbury et al.)] is the most widely recognized system used today. In this system of classification, based on morphological characteristics methane-utilizing bacteria are divided into five groups. They are: Methylosinus, Methylocystis, Methylomonas, Methylobacter and Methylococcus. Bacteria of these five groups reported by Whittenbury et al. utilize methane, dimethyl ether, and methanol for growth energy and they were all reported as strictly aerobic and gram-negative.

As one specific embodiment of the present invention it has been discovered that $C_3$-$C_6$ methyl ketones are produced by contacting the corresponding $C_3$-$C_6$alkanes or $C_3$-$C_6$ secondary alcohols under aerobic conditions with resting microbial cells derived from obligate or facultative methylotrophic microorganisms or enzyme preparations derived from said cells, wherein said microorganisms have been previously grown under aerobic conditions in a nutrient medium containing methane. In this process, secondary alcohols are also produced from the $C_3$-$C_6$ alkanes.

As another specific embodiment of the present invention it has been discovered that $C_3$-$C_6$ methyl ketones can be produced by contacting the corresponding $C_3$-$C_6$ secondary alcohols under aerobic conditions with microbial cells (preferably resting microbial cells) derived from obligate or facultative methylotrophic microorganisms or enzyme preparations derived from said cells, wherein said microorganisms have been previously grown under aerobic conditions in a nutrient medium containing methanol.

Surprisingly, it has been found that the microbial cells or their enzyme preparations wherein the cells have been previously grown on methanol as the major carbon and energy source are capable of converting $C_3$-$C_6$ secondary alcohols to the corresponding methyl ketones, but they are not capable of converting the $C_3$-$C_6$ alkanes to the corresponding methyl ketones. The methane-grown microbial cells or their enzyme preparations are capable of converting both $C_3$-$C_6$ alkanes and $C_3$-$C_6$ secondary alcohols to the corresponding methyl ketones.

The $C_3$-$C_6$ alkanes used in the process of the invention are preferably linear n-alkanes, e.g., propane, n-butane, n-pentane and n-hexane, most preferably the alkanes are either propane or n-butane. The $C_3$-$C_6$ secondary alcohols are preferably derived from linear $C_3$-$C_6$ alkanes, most preferably 2-propanol and 2-butanol.

Another particular preferred embodiment of the invention includes a process for converting $C_3$-$C_6$ linear secondary alcohols to the corresponding methyl ketones by contacting a $C_3$-$C_6$ linear secondary alcohol under aerobic conditions with an enzyme preparation comprising the novel $C_3$-$C_6$ secondary alcohol dehydrogenase (SADH) enzyme (in the form of a crude extract, purified form or immobilized form) in combination with nicotinamide adenine dinucleotide $NAD^+$).

The instant invention includes the following features:

Resting-cell suspensions of the new $C_1$-utilizing microbes oxidize (dehydrogenate) $C_3$-$C_6$ secondary alcohols to their corresponding methyl ketones. The product methyl ketones accumulate extracellularly. Among the secondary alcohols, 2-butanol was oxidized at the highest rate.

Succinate-grown cells of the new facultative methylotrophs isolates do not convert secondary alcohols to methyl ketones.

Some enzymatic degradation of 2-butanone was observed. The product, 2-butanone, did not inhibit the conversion of 2-butanol to the corresponding 2-butanone. The rate of the 2-butanone production was linear for the first four hours of incubation for the cultures tested.

A yeast culture had the highest production rate and had a higher temperature optimum (40° C.) and there was a reasonably high 2butanone production rate at 45° C. (The bacteria had a temperature optimum of about 35° C.)

Metal-chelating agents inhibit the production of 2-butanone which suggests the involvement of metal(s).

Secondary alcohol dehydrogenase activity was found in the cell-free soluble extract of the sonically disrupted cells of the $C_1$-grown isolates. The cell-free system requires a cofactor, specifically $NAD^+$, for its activity. The new secondary alcohol dehydrogenase specifically and stoichiometrically oxidizes $C_3$-$C_6$ secondary alcohols to their corresponding methyl ketones. The enzyme has been purified 2,600 fold and shows a single protein band on acrylamide gel electrophoresis. It has a molecular weight of 95,000 dalton. The bacterial SADH consists of two subunits of 48,000 dalton and two atoms of zinc per molecule of enzyme protein. Primary alcohols are not converted to ketones by the SADH. The pH and temperature optima for SADH are 8–9, and 30°–35° C., respectively. The activation energy calculated is 19.8 K cal. Acrylamide gel electrophoresis of the purified SADH fraction stained with coomassie brilliant blue and activity stain, as well as the crude soluble cell-free extracts from distinct types of methanol-grown microbes stained with activity stain were compared. Both the protein stain and the enzyme activity stain of the purified SADH showed a single protein band. The mobility on the gel electrophoresis of SADH from the distinct types of methanol-grown bacterial cells were identical. Yeast SADH had faster mobility toward anode on the gel electrophoresis. The addition of substrates in the SADH reaction does not require an obligatory order. The SADH activity is inhibited by metal-chelating agents, by strong thio-reagents, and by the product 2-butanone.

Cell suspensions of yeasts grown on methyl radical donating compounds (e.g., methanol, methylamine, methyl formate, etc.) catalyze the conversion of secondary alcohols to the corresponding methyl ketones.

Cell suspensions of yeasts of the invention grown on methyl radical donating compounds (e.g., methanol, methylamine, methyl formate, etc.) catalyze the conversion of secondary alcohols to the corresponding methyl ketones.

Cell-free extracts derived from methyl-radical (e.g., methanol)-grown yeasts of the invention catalyzed an $NAD^+$-dependent oxidation of $C_3$-$C_6$ secondary alcohols to the corresponding methyl ketones. The purified $NAD^+$-specific secondary alcohol dehydrogenase from methanol-grown yeast of the invention is homogeneous as judged by polyacrylamide gel electrophoresis. The purified enzyme catalyzes the conversion of secondary alcohols to the corresponding methyl ketones in the presence of $NAD^+$ as an electron acceptor. Primary alcohols were not oxidized by the purified enzyme. The optimum pH for conversion of secondary alcohols by the purified yeast-derived enzyme is 8. The molecular weight of the purified yeast-derived SADH as determined by gel filtration is $98,000 \pm 3,000$ and subunit size as determined by sodium dodecyl sulfate gel electrophoresis is 48,000. The activity of the purified yeast-derived SADH was inhibited by sulfhydryl inhibitors and metal-binding agents.

$C_3$-$C_6$ n-alkanes are converted to $C_3$-$C_6$ secondary alcohols by cell suspensions of the methane-grown methylotrophs and the secondary alcohols accumulate extracellularly. Other microorganisms, e.g., yeasts, actinomycetes, and fungi, grown on $C_1$-compounds will oxidize the $C_3$-$C_6$ n-alkanes to the corresponding secondary alcohols.

$C_3$-$C_6$ n-alkanes are converted to $C_3$-$C_6$ sec. alcohols by cell-free particulate fractions derived from the methylotrophic microorganisms of the invention. The reaction requires oxygen and reduced nicotinamide adenine dinucleotide (NADH) as electron donor. The conversion of the n-alkanes to the sec. alcohols is inhibited by thio-containing compounds and metal-binding agents such as $\alpha,\alpha$-bipyridyl, thiosemicarbazide, thiourea, 1,10-phenanthroline, and 8-hydroxyquinoline. (This suggests the involvement of metal ion(s) in the oxidation of $C_3$-$C_6$ n-alkanes to sec. alcohols.) The hydroxylation of $C_3$-$C_6$ n-alkanes to the corresponding sec. alcohols is inhibited in the presence of propylene. This suggests that the propylene and n-alkanes (e.g., propane) are competing for the same enzyme system(s). Ascorbate and reduced nicotinamide adenine dinucleotide phosphate (NADPH) could also be utilized as electron donor in place of NADH for hydroxylation of n-alkanes to the corresponding sec. alcohols.

A preferred group of methane-utilizing methylotrophic microorganisms include those microorganisms derived from the genera: Methylosinus; Methylocystis; Methylomonas; Methylobacter; Methylococcus; and Methylobacterium.

A preferred group of methanol-utilizing methylotrophic microorganisms include those microorganisms derived from the genera: Methanomonas; Pseudomonas; Bacterium; Hyphomicrobium; Achromabacter; Protaminobacter; Vibrio; Rhodopseudomonas; Bacillus; Brevibacterium; Candida; and Hansenula.

The classification system of methane-oxidizing bacteria proposed by R. Whittenbury, K. C. Phillips and J. F. Wilkinson (*J. Gen. Microbiology*, 61, 205-218 (1970) hereinafter Whittenbury et al.) is the most widely recognized system used today. In this system of classification, on the basis of morphological characteristics methane-utilizing bacteria are divided into five groups. They are: Methylosinus, Methylocystis, Methylomonas, Methylobacter and Methylococcus. Bacteria of these five groups reported by Whittenbury et al. utilize methane, dimethyl ether, methanol, methyl formate and methyl carbonate for growth energy and they were all reported as strictly aerobic and Gram-negative. They are also characterized as being non-endosporing, i.e., the ability to form cysts and exospores with complex fine structure and complex internal structure.

The methylotrophic microorganisms reported by Whittenbury et al. (the disclosure of which is incorporated herein by reference) are contemplated for use in the practice of the present invention. Specifically, one may use those methane-utilizing methylotrophic microorganisms mentioned in Table 4, page 214 of the Whittenbury et al. paper, i.e., those microorganisms identified as: *Methylosinus trichosporium, Methylosinus sporium, Methylocystis parvus, Methylomonas methanica, Methylomonas albus, Methylomonas streptobacterium, Methylomonas agile, Methylomonas rubrum, Methylomonas rosaceus, Methylobacter chroococcum, Methylobacter bovis, Methylobacter capsulatus, Methylobacter vinelandii, Methylococcus capsulatus* (including *Methylococcus capsulatus* Strain Bath referred to by J. Colby and H. Dalton, *J. Biochem.*, 157, 495-497 (1976)) and *Methylococcus capsulatus* Strain Texas referred to by D. W. Ribbons, *J. Bacteriol.*, 122, 1351-1363 (1975)), and *Methylococcus minimus*. These methylotrophic microorganisms may be used in the form of their whole cells, enzyme extracts thereof or immobilized preparations of those whole cells or enzyme extracts, such as by use of DEAE cellulose or ion exchange resin or porous alumina carriers. In those instances where the oxidative enzyme system accumulates or is closely associated with the cells' membrane, in some instances it is preferred to use the enzyme in its cell-bound form.

Subcultures of some methylotrophic miroorgnisms described by Whittenbury et al. have been deposited with the official depository of the United States Department of Agriculture, Agriculture Research Service, Northern Regional Research Laboratory, Peoria, Illinois 61604 by depositing therein subcultures of each, and have received from the depository the individual NRRL strain designations as indicated below. These subcultures have been deposited in accordance with the procedures of the Department of Agriculture without any restriction such that progency of these strains are available to the public, including but not limited to those citizens in the United States of America and those citizens in West Germany. Strains of methylotrophic microorganisms deposited are identified below:

| Culture | | USDA Agricultural Research Service Designation |
|---|---|---|
| *Methylosinus trichosporium* | OB3b | NRRL B-11,196 |
| *Methylosinus sporium* | 5 | NRRL B-11,197 |
| *Methylocystis parvus* | OBBP | NRRL B-11,198 |
| *Methylomonas methanica* | $S_1$ | NRRL B-11,199 |
| *Methylomonas albus* | BG8 | NRRL B-11,200 |
| *Methylobacter capsulatus* | Y | NRRL B-11,201 |

Progency of these strains are available to anyone who requests the same without any restriction as to availability. Subcultures of the aforementioned strains were originally obtained from R. Whittenbury, Department of Biological Science, University of Warwick, Warwickshire, Conventry, England.

The morphological and taxonomical chracteristics of the above-mentioned methylotrophic strains are as follows:

Methylosinus trichosporium: OB3b, NRRL B-11,196

Produces white colonies on salt agar plates in the presence of methane or methanol. The organisms are motile, rod-shaped, gram-negative and aerobic. Rosettes are frequently formed. Has a Type II membrane structure.

Methylosinus sporium: 5, NRRL B-11,197

Produces white colonies on salt agar plates in the presence of methane or methanol. The organisms are motile, rod-shaped, gram-negative and aerobic. Rosettes are frequently formed. Organisms form exospores which are heat-resistant; spores budded off the non-flagellated poles of the organisms which assumed a vibrio shape. Organic compounds other than methane and methanol do not support growth. Has a Type II membrane structure.

Methylocystis parvus: OBBP, NRRL B-11,198

Produces mucoid white colonies on salt agar plates in the presence of methane or methanol. The organisms are non-motile, coco-bacillus in shape, gram-negative and aerobic. Organisms form cysts which are dessication-resistant, but not heat resistant. Grows at the expense of methane or methanol. Organic compounds other than membrane and methanol do not support growth. Has a Type II membrane structure.

Methylomonas methanica: $S_1$, NRRL B-11,199

Produces pink colonies on salt-agar plates in the presence of methane or methanol. The organisms are motile, rod-shaped, gram-negative and aerobic. Produce slimy capsules. They grow at the expense of methane and methanol. Organic compounds other than methane and methanol do not support growth. Has a Type I membrane structure.

Methylomonas albus: BG8, NRRL B-11,200

Produces white colonies on salt-agar plates in the presence of methane or methanol. The organisms are motile, rod-shaped, gram-negative and aerobic. Produces slimy capsule. Grows at the expense of methane and methanol. Organic compounds other than methane and methanol do not support growth. Has a Type I membrane structure.

Methylobacter capsulatus: Y, NRRL B-11,201

Produces white to brown colonies on salt-agar plates in the presence of methane or methanol. The organisms are motile, rod-shaped, gram-negative and aerobic. Produces slimy capsule. Grows at the expense of methane and methanol. Organic compounds other than methane and methanol do not support growth. Has a Type I membrane structure.

Recently, Patt, Cole and Hanson (*International J. Systematic Bacteriology*, 27 (2) 226-229 (1976)) disclosed that methylotrophic bacteria are those bacteria that can grow non-autotrophically using carbon compounds containing one or more carbon atoms, but containing no carbon-carbon bonds. Patt et al have proposed that methylotrophs should be considered "obligate" if they are capable of utilizing only carbon compounds containing no carbon-carbon bonds (e.g., methane, methanol, dimethyl ether, methylamine, etc.) as the sole sources of carbon and energy whereas "facultative" methylotrophs are those organisms that can use compounds containing no carbon-carbon bonds and complex compounds containing carbon-carbon bonds as the sole sources of carbon and energy. In their paper, Patt et al. disclosed a methane-oxidizing bacterium, which they identified as *Methylobacterium organophilum sp. nov.* (ATCC 27,886). This bacterium presumably differs from all previously described genera and species of methane-utilizing bacteria because of its ability to utilize a variety of organic substrates with carbon-carbon bonds as sources of carbon and energy.

As another embodiment of the present invention, it has been discovered that this microorganism (*Methylobacterium organophilum sp.* nov. ATCC 27,886) and other methane- or methanol-grown facultative methylotrophic microorganisms are also capable of oxidizing the $C_3$-$C_6$ alkanes and $C_3$-$C_6$ secondary alcohols. In other words, they possess oxidative (and alcohol dehydrogenase) enzyme activity when cultivated in the presence of methane or methanol (in the case of the alcohol dehydrogenation). As discussed above with respect to the Whittenbury et al. methane-utilizing methylotrophic microorganisms, the facultative methylotrophs may be used in the form of their soluble extract or be placed in immobilized form or used in the cell-bound form when put to use in the process of the present invention.

Other known methane-utilizing methylotrophic strains may be used in the process of the present invention, e.g., *Methylomonas sp.* AJ-3670 (FERM P-2400) referred to in U.S. Pat. No. 3,930,947 as freely available from the Fermentation Research Institute, Agency of Industrial Science and Technology, Ministry for Industrial Trade and Industry, Chiba, Japan; and *Methylococcus* 999 referred to in U.S. Pat. No. 4,042,458 as having NCIB Accession No. 11083 as well as *Methylomonas* SM3 having NCIB Accession No. 11084 (which has been described in Netherlands patent application No. 74/16644). Mixtures of methylotrophic and non-methylotrophic microorganisms may be utilized, such as the systems described in U.S. Pat. Nos. 3,996,105 and 4,042,458.

Prior art workers have described various obligate and facultative methanol-utilizing methylotrophic microorganisms (i.e., those methylotrophs which are not capable of growing on methane). Microbial cells derived from these previously described microorganisms and their enzyme preparations wherein the microorganisms have been grown on methanol are capable of converting $C_3$-$C_6$ secondary alcohols to the corresponding methylketones. Specific methanol-utilizing methylotrophic microorganisms, described by prior art workers, useful in the practice of the present invention are described below.

Obligate Methanol-Utilizing Methylotrophic Microorganisms

*Methanomonas methylovora*, ATCC 21,852 (k. Kouno et al, *J. Gen. and Appl. Microbiol.*, 19, 11 (1973)). The organisms are Gram-negative, motile, non-spore-forming. The organisms only grow on methanol and methylamine. Methane does not support growth. *Pseudomonas sp.*, ATCC 21, 439. The organisms are white, Gram-negative and motile. They grow on methanol and methylamine, but not on methane.

*Pseudomonas $w_1$* (J. S. Dahl et al., *J. Bacteriol.*, 109, 916 (1972)). The organisms are Gram-negative, motile, non-spore-forming. The organisms only grow on methanol and methylamine. Methane does not support growth.

*Bacterium $C_2A_1$* (J. Colby and L. J. Zatman, *J. Biochem.*, 132, 101 (1973)). The organisms are Gram-negative. The organisms only grow on methanol and methylamine. Methane does not support growth.

*Bacterium 4B6* (J. Colby and L. J. Zatman, *J. Biochem.*, 132, 101 (1973)). The organisms are Gram-negative and motile. The organisms only grow on methylamine. Methane, methanol and other organic compounds do not support growth.

*Hyphomicrobium sp.* (N. Takada et al., *Proc. Japan Soc. for Ferment. Tech.*, p. 72 (1973)). The organisms are colorless, stalked bacteria which grow by budding from the ends of hyphae. The organisms grow on methanol and methylamine. Methane does not support growth.

*Achromobacter sp.* (S. Kubasawa et al., *Proc. Japan Soc. for Agricultural Chem.*, p. 344 (1970)). The organisms are Gram-negative, non-spore-forming and motile. The organisms only grow on methanol. Methane does not support growth.

Facultative Methanol-Utilizing Methylotrophic Microorganisms

*Pseudomonas sp.* ATCC 21,438. The organisms are pink, Gram-negative and motile. They grow on methanol, methylamine and other organic compounds, but not methane.

*Pseudomonas $AM_1$* (Peel and Ouayle, *J. Biochem.*, 81, 465 (1961)). The organisms are Gram-negative, pink, motile and non-spore-forming. The organisms grow on methanol, methylamine, methyl formate and other organic compounds, but do not grow on methane.

*Hyphomicrobium sp.* (Hirsh and Conti, *Arch. Mikrobiol.*, 62, 289 (1968)). The organisms are colorless, stalked bacteria growing by budding from ends of hyphae. The organisms grow on methanol, methylamine, methyl formate and other organic compounds, but do not grow on methane.

Protaminobacter ruber (Stocks and McCleskey, *J. Bacteriol.*, 88, 1065 (1964)). The organisms are red, Gram-negative and motile. The organisms grow on methanol, methylamine, methyl formate and organic compounds, but do not grow on methane.

*Vibrio extroquens* (Bassalik, *Jb. Wiss Bot.*, 53, 255 (1913)). The organisms are red, motile, Gram-negative. The organisms grow on methanol, methyl formate and other organic compounds, but do not grow on methane.

*Rhodopseudomonas acidophila* (H. Sahm et al., *J. Gen. Microbiol.*, 94, 313 (1976)). The organisms are Gram-negative. The organisms grow anaerobically in the presence of light on methanol and other organic compounds, but do not grow on methane.

*Pseudomonas MS* ATCC 25,262 (H. F. Kung and C. Wagner, *Biochem. J.*, 116, 357 (1970)). The organisms are Gram-negative, motile and non-spore-forming. The organisms grow on methanol, methylamine and other organic compounds, but do not grow on methane.

*Achromobacter rufescens* (T. Akiba et al, *J. Fermentation Technology*, 48, 323 (1970)). The organisms are Gram-negative, motile and non-spore-forming. The organisms grow on methanol and other organic compounds, but do not grow on methane.

*Bacillus soraceus* (T. Akiba et al, *J. Fermentation Technology*, 48, 323 (1970)). The organisms are Gram-positive and non-motile. The organisms grow on methanol and other organic compounds, but do not grow on methane.

*Brevibacterium sp.* (Japanese Patent Publication No. 48-77083 to Fukimbara et al. (1973)). The organisms are Gram-negative and non-spore-forming. The organisms grow on methanol and other organic compounds, but do not grow on methane.

*Pseudomonas* $M_{27}$ (C. Anthony and L. J. Zatman, *Biochem. J.*, 92, 609 (1964)). The organisms are Gram-negative, motile and non-spore-forming. The organisms grow on methanol, methylamine, methyl formate and other organic compounds, but do not grow on methane.

*Pseudomonas C* (Y. Chalfan and R. I. Mateles, *Appl. Microbiol.*, 23, 135 (1972)). The organisms are Gram-negative, motile and non-spore-forming. The organisms grow on methanol, methyl formate and other organic compounds, but do not grow on methane.

Prior art workers have also described various facultative methanol-utilizing methylotrophic yeasts (i.e., yeasts are not capable of growing on methane). Microbial cells derived from these previously described yeasts and their enzyme preparations (particularly the cell-free extracts containing SADH enzyme activity and NAD+), wherein the yeasts' microorganisms have been grown on methanol or similar $C_1$-compound (i.e., methyl-radical donating compound) are capable of converting under aerobic conditions $C_3$–$C_6$ secondary alcohols to the corresponding methyl ketones.

Specific $C_1$ compound utilizing methylotrophic yeasts, described by prior art workers, useful in the practice of the present invention are: *Candida utilis* ATCC 26387; *Candida utilis* NRRL Y-660; *Hansenula polymorpha* ATCC 26012; *Hansenula polymorpha* NRRL Y-2214; *Hansenula polymorpha* NRRL Y-2267; *Hansenula anomala* NRRL Y-336; *Pichia pastoris* NRRL Y-55; *Pichia pastoris* NRRL Y-7556.

In addition, the following newly isolated yeasts may be used in the practice of the invention:

| Strain Name | ER & E Designation | U.S.D.A. Agriculture Research Center and Designation |
|---|---|---|
| *Pichia sp.* | CRL-72 | NRRL Y-11,328 |
| *Torulopsis sp.* | $A_1$ | NRRL Y-11,419 |
| *Kloeckera sp.* | $A_2$ | NRRL Y-11,420 |

These new yeasts isolates have the following taxonomical characteristics:

*Pichia sp.* CRL-72 (NRRL Y-11,328) Produces slimy white colonies on plates. Cells are large and oval; some cells have buds. Reproduce by budding and they grow aerobically on $C_1$–$C_6$ primary alcohols, $C_1$–$C_4$ primary amines, methyl formate, succinate and nutrient agar. They do not grow on methane.

*Torulopsis sp.* $A_1$ (NRRL Y-11,419) Capable of growth on methanol, methyl formate, methylamine, ethanol, propylamine, and nutrient agar. Does not grow on methane. Cells are large oval shape and show multilateral budding under microscopic examination.

*Kloeckera sp.* $A_2$ (NRRL Y-11,420) Capable of growth on methanol, methyl formate, methylamine, ethanol, propylamine, and nutrient agar. Does not grow on methane. Cells are large oval shape and show bipolar budding under microscopic examination.

In addition to the newly isolated yeasts described above, the new bacteria strains disclosed and claimed in U.S. Ser. No. 896,476, filed Apr. 14, 1978 (the disclosure of which is incorporated herein by reference) may be used in the practice of the invention.

Typical bacteria strains that are disclosed in said application are identified as follows:

| Methylotrophic Strain Name | ER & E Designation | U.S.D.A. Agriculture Research Center Designation |
|---|---|---|
| *Methylosinus trichosporium* | CRL 15 PM1 | NRRL B-11,202 |
| *Methylomonas streptobacterium* | CRL 17 PM3 | NRRL B-11,208 |
| *Methylomonas agile* | CRL 22 PM9 | NRRL B-11,209 |
| *Methylococcus capsulatus* | CRL M1 | NRRL B-11,219 |
| *Methylobacterium organophilum* | CRL 26 R6 | NRRL B-11,222 |

The above new strains have been deposited at the United States Department of Agriculture, Agriculture Research Service, Northern Regional Research Laboratory (NRRL), Peoria, Illinois 61604 and have received from NRRL the individual NRRL designations as indicated above pursuant to a contract between NRRL and the assignee of this patent application (Exxon Research and Engineering Company (ER&E)). The contract with NRRL provides for permanent availability of the progeny of these strains to the public including citizens of West Germany, upon the issuance of the U.S. patent or the publication of a German patent application corresponding to this application, whichever comes first, occurs and that progeny of these strains will be made available to one determined by the U.S. Commissioner of Patents and Trademarks to be entitled thereto according to 35 USC 122 and the Commissioner's rules pertaining thereto (including 37 CRF 1.14, with particular reference to 886 OG 638) or the West German Patent Office. The assignee of the present application has agreed that, if any of these strains on deposit should die, or is destroyed, during the effective life of the patent, it will be replaced with a living strain of the same organism.

It will be understood that mutants of these bacteria and yeasts may also be used in producing microbial cells and enzyme preparations derived from these cells.

The maintenance of the cultures of these newly discovered and isolated strains should be carefully controlled. The preferred means for maintaining the cultures is described below.

MAINTENANCE OF CULTURES

The organisms are preferably subcultured every two weeks on mineral salts agar plates which contain medium described in Example 1. In the case of yeast cells, yeast nitrogen base is added to the above medium.

These plates should be incubated in glass dessicators which have lids with an airtight seal and external sleeves with a tooled hose connection. Dessicators are to be evacuated and filled with a gas mixture of methane and air (1:1 v/v). Incubation should be at 30° C. Cultures will survive in these dessicators for three months at 4° C. However, frequent transfer of cultures is preferred.

In commercial processes for the propagation of microorganisms, it is generally necessary to proceed by stages. These stages may be few or many, depending on the nature of the process and the characteristics of the microorganisms. Ordinarily, propagation is started by inoculating cells from a slant of a culture into a presterilized nutrient medium usually contained in a flask. In the flask, growth of the microorganisms is encouraged by various means, e.g., shaking for thorough aeration, and maintenance of suitable temperature. This step or stage is repeated one or more times in flasks or vessels containing the same or larger volumes of nutrient medium. These stages may be conveniently referred to as culture development stages. The microorganisms with or without accompanying culture medium, from the last development stage, are introduced or inoculated into a large scale fermentor to produce commercial quantities of the microorganisms or enzymes therefrom.

Reasons for growing the microorganisms in stages are manyfold, but are primarily dependent upon the conditions necessary for the growth of the microorganisms and/or the production of enzymes therefrom. These include stability of the microorganisms, proper nutrients, pH, osmotic relationships, degree of aeration, temperature and the maintenance of pure culture conditions during fermentation. For instance, to obtain maximum yields of the microbial cells, the conditions of fermentation in the final stage may have to be changed somewhat from those practiced to obtain growth of the microorganisms in the culture development stages. Maintaining the purity of the medium, also, is an extremely important consideration, especially where the fermentation is performed under aerobic conditions as in the case of the methylotroph microorganisms. If the fermentation is initially started in a large fermentor, a relatively long period of time will be needed to achieve an appreciable yield of microorganisms and/or oxidative and dehydrogenase enzymes therefrom. This, of course, enhances the possibility and contamination of the medium and mutation of the microorganisms.

The culture media used for growing the methylotrophic microorganisms and inducing the oxidative enzyme system will be comprised of inorganic salts of phosphate, sulfates and nitrates as well as oxygen and a source of $C_1$ compounds. The fermentation will generally be conducted at temperatures ranging from 5° to about 50° C., preferably at temperatures ranging from about 25° to about 45° C. The pH of the culture medium should be controlled at a pH ranging from about 4 to 9 and preferably from about 5.5 to 8.5 and more preferably from 6.0 to 7.5. The fermentation may be conducted at atmospheric pressures although higher pressures up to about 5 atmospheres and higher may be employed.

Typically, to grow the methylotrophic microorganisms and to induce the oxygenase and dehydrogenase enzymes, the microorganisms are inoculated into the medium which contains the enzyme-inducing growth and energy substrate (e.g., methane, methanol, methylamine, etc.) and oxygen. If methane is the inducing growth substrate, it may be supplied in the form of natural gas. For continuous flow culture the microorganisms may be grown in any suitably adapted fermentation vessel, for example, a stirred baffled fermentor or sparged tower fermentor, which is provided either with internal cooling or an external recycle cooling loop. Fresh medium may be continuously pumped into the culture at rates equivalent to 0.02 to 1 culture volume per hour and the culture may be removed at a rate such that the volume of culture remains constant. The inducer-growth substrate-oxygen mixture and possibly carbon dioxide or other gases is contacted with the medium preferably by bubbling continuously through a sparger at the base of the vessel. The source of oxygen for the culture may be air, oxygen or oxygen-enriched air. Spent gas may be removed from the head of the vessel. The spent gas may be recycled either through an external loop or internally by means of a gas inducer impeller. The gas flows and recycle should be arranged to give maximum growth of microorganism and maximum utilization of the inducing-growth substrate. When methane or methanol is the inducing-growth substrate the amount of methane or methanol ranges from 0.2 to about 2% V/V. In the case of other inducing growth substrates such as methylamine the amount will be about 0.4% V/V.

The microbial cells may be harvested from the growth medium by any of the standard techniques commonly used, for example, flocculation, sedimentation and/or precipitation, followed by centrifugation and/or filtration. The biomass may also be dried, e.g., by freeze or spray drying and may be used in this form for further use in the oxidative and/or alcohol dehydrogenase conversion process. In the case of obtaining an oxidative enzyme system (i.e., methane-induced cells) the enzyme is generally closely associated with the cell's membranes and it may be desirable to use the microbial cells as the enzyme source. In the case of the alcohol dehydrogenase enzyme system one may conveniently use the enzyme in the form of the soluble extract (which may be optionally immobilized onto an inert carrier).

Stated another way, in the case of obtaining the oxygenase enzyme system which is obtainable from the methane-induced cells (not methanol, methylamine, etc.) for use in aerobically converting lower alkanes to secondary alcohols and methyl ketones, one may use the intact cells themselves or the cell-free particulate fraction of the cells. The latter cell-free particulate fraction is the material which precipitates when the supernatant after centrifuging broken cells at 10,000×g. for 30 min. is centrifuged for 1 hour at 10,000×g. or greater. On the other hand, when it is desired to obtain the secondary alcohol dehydrogenase (SADH) enzyme fraction one first breaks the cells, e.g., sonication, etc., secondary removes the cellular debris, e.g., centrifuges at 10,000×g. for about 20 minutes and the recovered crude SADH enzyme can thereafter be further purified by mild heat treatment, column chromatography, etc., as described in the examples below. The SADH enzyme occurs in the supernatant fraction of the centrifuged broken cells whereas the oxygenase enzyme (i.e., the cells induced by methane) occurs in the particulate fraction as described above.

To put the invention to practice, the oxidative and/or alcohol dehydrogenase enzyme system is obtained, such as, for example, in the manner described above wherein the microbial cells derived from the methylotrophic microorganisms which have been aerobically grown in a nutrient medium containing the inducing growth substrate or enzyme preparations derived therefrom. The source of the enzyme is not critical, but it is preferred to obtain such a preparation from one of the induced obligate or facultative methylotrophic microorganisms described above. The nutrient medium for which the microorganisms is induced and grown may be the one described by Whittenbury et al. or more preferably the culture medium described by Foster and Davis, *J. Bacteriol.*, 91, 1924–1931 (1966). Once the microorganisms have been induced and grown, and the microbial cells are preferably harvested, washed and the resulting resting microbial cells or the resulting enzyme preparation may then be used as such to convert $C_3$-$C_6$ alkanes to the corresponding secondary alcohols or methyl ketones or to convert $C_3$-$C_6$ secondary alcohols to the corresponding methyl ketones under aerobic conditions (in the presence of oxygen) in a buffered solution. The mixture of the substrate material and induced, resting microbial cells or enzyme preparation in the buffered solution is incubated until the desired degree of conversion has been obtained. Thereafter, the ketone product is recovered by conventional means, e.g., distillation, etc.

To facilitate the necessary effective contact of oxygen and the enzyme system (whether it be an enzyme preparation as such or microbial cells derived from the induced methylotrophic microorganisms), it is preferred, for best results, to employ a strong, finely divided air stream into a vigorously stirred dispersion of the substrate ($C_3$-$C_6$ alkane or $C_3$-$C_6$ secondary alcohol) in the oxidation medium that generally contains water and a buffer, and in which the enzyme preparation or induced microbial cell system is suspended. The enzyme preparation or induced microbial cell system may then be separated from the liquid medium, preferably by filtration or centrifugation. The resulting ketone may then generally be obtained.

The process of the invention may be carried out batchwise, semi-continuously, continuously, concurrently or countercurrently. Optionally, the suspension containing the enzyme preparation or methylotrophic microorganisms and buffer solution is passed downwardly with vigorous stirring countercurrently to an air stream rising in a tube reactor. The top layer is removed from the downflowing suspension, while culture and remaining buffer solution constituents are recycled, at least partly, with more oxidative substrate and addition of fresh enzyme preparation or induced microbial cell system, as required.

The growth of the methylotrophic microorganisms and the oxidation process may be conveniently coupled by conducting them simultaneously, but separately and using much higher aeration in the oxidation process (e.g., an air excess of at least twice that required for growth, preferably at least five times as much aeration). Both the growth process, the oxidative or dehydrogenating processes may be conducted in the same reactor in sequential or simultaneous operations by alternate use of normal and strong aeration.

The invention is illustrated further by the following examples which, however, are not to be taken as limiting in any respect. All parts and percentages, unless expressly stated otherwise, are by weight.

EXAMPLE 1

A nutrient medium as described by Foster and Davis, *J. Bacteriol.*, 91, 1924–1931 (1966) having the following composition per liter was prepared:

$Na_2HPO_4$: 0.21 g.
$NaH_2PO_4$: 0.09 g.
$NaNO_3$: 2.0 g.
$MgSO_4.7H_2O$: 0.2 g.
KCl: 0.04 g.
$CaCl_2$: 0.015 g.
$FeSO_4.7H_2O$: 1 mg.
$CuSO_4.5H_2O$: 0.01 mg.
$H_3BO_4$: 0.02 mg.
$MnSO_4.5H_2O$: 0.02 mg.
$ZnSO_4$: 0.14 mg.
$MoO_3$: 0.02 mg.

The pH of the nutrient medium was adjusted to 7.0 by the addition of acid or base and 50 ml. samples of the nutrient medium were charged into a plurality of 300 ml. shaker flasks. The shaker flasks were inoculated with an inoculating loop of cells from an agar plate containing homogeneous colonies of the microorganisms on the plate (the purity of the isolates was confirmed by microscopic examination). The isolates had been maintained on methanol (0.4% V/V) agar plates or on agar plates under an atmosphere of methane and air having a 1:1 V/V gas ratio which had been transferred every two weeks. For growth on methanol, the medium was supplemented with 0.4% methanol. For growth on methane, the gaseous phase of the inoculated flasks was replaced with a gas mixture comprised of methane and air having a ratio of 1:1 on a V/V basis. The inoculated flasks were sealed air-tight and were incubated on a rotary shaker of orbital radius 2.5 cm. at 250 rpm and at 30° C. for two days until turbidity in the medium had developed. The cells were harvested by centrifugation at 10,000×g. at 4° C. for 30 minutes. The cell pellet was washed twice with a 0.05 M phosphate buffer at a pH of 7.0 (containing 0.02 M $MgCl_2$). The washed cells were then suspended in a 0.05 M phosphate buffer at pH 7.0.

A 0.5 ml. sample of each washed cell suspension (2 mg. cells) was put into 10 ml. vials at 4° C. which were sealed with a rubber cap. The gaseous phase of the vials was removed with vacuum and then was replaced with a gas mixture of the substrate reactant (i.e., alkane or secondary alcohol) and oxygen at a 1:1 V/V ratio. (In the case of a liquid substrate, i.e., secondary alcohol, 10 µl of the substrate was put in the 10 ml. vials). The vials were then incubated at 30° C. on a rotary shaker at 300 rpm. Samples of product (1–3 µl) were withdrawn periodically with a microsyringe and the products were analyzed by gas chromatography (ionization flame detector column).

Table I shows the conversion rates for the conversion of n-propane, n-butane, n-pentane and n-hexane to acetone, 2-butanone, 2-pentanone and 2-hexanone respectively by induced, resting (washed) microbial cell suspensions of several microorganisms, strains of which had been grown on methane by the experimental procedure described above. It can be seen from these data that the resting (washed) cells of the methane-grown microorganisms are capable of converting $C_3$–$C_6$ n-alkanes to the corresponding methyl ketones.

TABLE I

Conversion Rates For Oxidation of Hydrocarbons to Ketones by Cell-Suspensions of Methylotrophs Grown On Methane

| Methylotrophic Microorganism Strain Identification[b] | Conversion Rates[a] μmoles/hr/mg protein | | | |
|---|---|---|---|---|
| | n-Propane to Acetone | n-Butane to 2-Butanone | n-Pentane to 2-Pentanone | n-Hexane to 2-Hexanone |
| *Methylosinus trichosporium* OB3b (NRRL B-11,196) | 1.5 | 1.2 | 0.72 | 0.05 |
| *Methylosinus sporium* 5 (NRRL B-11,197) | 2.1 | 0.58 | — | — |
| *Methylocystis parvus* OBBP (NRRL B-11,198) | 1.8 | 1.0 | 0.51 | 0.04 |
| *Methylomonas methanica* S1 (NRRL B-11,199) | 2.5 | 0.30 | 0.28 | 0.02 |
| *Methylomonas albus* BG8 (NRRL B-11,200) | 2.7 | 0.60 | — | — |
| *Methylobacter capsulatus* Y (NRRL B-11,201) | 1.6 | 1.1 | 0.63 | 0.07 |
| *Methylococcus capsulatus* Texas (ATCC 19069) | 1.2 | 0.52 | 0.42 | 0.09 |
| *Methylobacterium organophilum* XX | 2.8 | 2.0 | 0.58 | 0.09 |

[a]The products were identified by gas chromatography retention time comparisons with authentic standards. Analysis also revealed that no further oxidation of the products occurred.
[b]The dry weight of the cells was about 0.2 gm/100 ml culture broth.

EXAMPLE 2

Microbiological Conversion of Secondary Alcohols to Ketones

The procedure in Example 1 was repeated wherein a plurality of the methane-utilizing methylotrophic microorganisms were each grown aerobically in a nutrient medium containing methane as the alcohol dehydrogenase enzyme inducer and as the major carbon and energy source for growth. The cells were harvested and washed as described in Example 1. The resting microbial cells of the induced methane-grown methane-utilizing methylotrophic microorganisms were then contacted with $C_3$–$C_6$ secondary alcohols in a buffered solution by the procedure of Example 1. The results of this series of experiments are shown in Table II.

TABLE II

Conversion Rates For Oxidation of Sec-Alcohols to Ketones by Resting Cell-Suspensions of Methylotrophs Grown on Methane

| Methylotrophic Microorganism Strain Identification[b] | Conversion Rates[a] μmoles/hr/mg protein | | | |
|---|---|---|---|---|
| | 2-Propanol to Acetone | 2-Butanol to 2-Butanone | 2-Pentanol to 2-Pentanone | 2-Hexanol to 2-Hexanone |
| *Methylosinus trichosporium* OB3b (NRRL B-11,196) | 0.25 | 3.7 | 2.7 | 0.07 |
| *Methylosinus sporium* 5 (NRRL B-11,197) | 0.30 | 3.0 | — | — |
| *Methylocystis parvus* OBBP (NRRL B-11,198) | 0.32 | 1.1 | 0.80 | 0.065 |
| *Methylomonas methanica* S1 (NRRL B-11,199) | 0.40 | 0.39 | 0.25 | 0.01 |
| *Methylomonas albus* BG8 (NRRL B-11,200) | 1.3 | 3.5 | — | — |
| *Methylobacter capsulatus* Y (NRRL B-11,201) | 0.15 | 0.84 | 0.5 | 0.1 |
| *Methylococcus capsulatus*, Texas (ATCC 19069) | 0.80 | 0.60 | 2.5 | 1.0 |
| *Methylobacterium organophilum* XX (ATCC 24886) | 0.5 | 2.5 | 0.82 | 0.12 |

[a]The products were identified by gas chromatography retention time comparisons with authentic standards. Analysis also revealed that no further oxidation of the products occurred.
[b]The dry weight of the cells was about 0.2 g/100 ml culture broth.

EXAMPLE 3

Microbiological Conversion of Secondary Alcohols to Ketones

In this example, the procedure in Example 1 was repeated except that a plurality of methane-utilizing methylotrophic microorganisms were each aerobically grown in a methanol-containing nutrient medium instead of a methane-containing medium. The nutrients in the medium were the same as indicated in Example 1 except that 0.4% V/V methanol was used as the alcohol dehydrogenase inducer and major source of carbon and energy for growth. Following growth, the cells were harvested and washed as described in Example 1.

The resting cells of the induced methanol-grown methylotrophic microorganisms were then contacted with secondary alcohols in a buffered solution by the procedure described in Example 1. The results of this series of experiments are shown in Table III.

TABLE III

Conversion Rates For Conversion of Sec-Alcohols to Ketones by Cell-Suspensions of Methylotrophs Grown on Methanol

| Methylotrophic Microorganism Strain Identification[b] | Conversion Rates[a] $\mu n$ moles/hr/mg protein | | | |
|---|---|---|---|---|
| | 2-Propanol to Acetone | 2-Butanol 2-Butanone | 2-Pentanol to 2-Pentanone | 2-Hexanol to 2-Hexanone |
| Methylosinus trichosporium OB3b (NRRL B-11,196) | 0.30 | 4.1 | 2.9 | 0.9 |
| Methylosinus sporium 5 (NRRL B-11,197) | 0.45 | 3.5 | — | — |
| Methylocystis parvus OBBP (NRRL B-11,198) | 0.25 | 1.0 | 0.82 | 0.05 |
| Methylomonas methanica S1 (NRRL B-11,199) | 0.35 | 0.40 | 0.45 | 0.04 |
| Methylomonas albus BG8 (NRRL B-11,200) | 1.5 | 3.0 | — | — |
| Methylobacter capsulatus Y (NRRL B-11,201) | 0.52 | 1.5 | 0.60 | 0.12 |
| Methylococcus capsulatus, Texas (ATCC 19069) | 0.75 | 0.70 | 3.5 | 1.3 |
| Methylobacterium organophilum XX (ATCC 27886) | 0.70 | 2.8 | 0.9 | 1.1 |

[a]The products were identified by gas chromatography retention time comparisons with authentic standards. Analysis also revealed that no further conversion of the products occurred.
[b]The dry weight of the cells was about 0.2 g/100 ml culture broth.

EXAMPLE 4

Microbiological Conversion of Secondary Alcohols to Ketones

In this example, microbial cells of methanol-utilizing methylotrophic microorganisms, grown on methanol, were used to convert secondary alcohols to methyl ketones.

The procedure in Example 1 was repeated except that a plurality of methanol-utilizing methylotrophic microorganisms were each aerobically grown in a methanol-containing nutrient medium instead of a methane-containing medium. The nutrients in the medium were the same as indicated in Example 1 except that 0.4% V/V methanol was used as the alcohol dehydrogenase inducer and as the major carbon and energy source for growth. The cells were harvested and washed as described in Example 1. The resting microbial cells of the induced methanol-grown methanol-utilizing methylotrophic microorganisms were then contacted with C$_3$–C$_6$ secondary alcohols in a buffered solution by the procedure of Example 1. The reaction products were analyzed by gas chromatography and were found to contain 2-ketones as indicated in Table IV. The results of this series of experiments are shown in Table IV.

TABLE IV

Conversion Rates For Conversion of Sec-Alcohols to Ketones by Cell-Suspension of Methanol-Grown Obligate and Facultative Methanol-Utilizing Methylotrophs

| Methylotrophic Microorganism Strain Identification[b] | Conversion Rates[a] $\mu$moles/hr/mg protein | | | |
|---|---|---|---|---|
| | 2-Propanol to Acetone | 2-Butanol to 2-Butanone | 2-Pentanol to 2-Pentanone | 2-Hexanol to 2-hexanone |
| Pseudomonas MS ATTC 25262 (Facultative) | 0.80 | 3.5 | 2.1 | 0.80 |
| Pseudomonas sp. ATCC 21438 (Facultative) | 0.45 | 3.2 | 2.7 | 0.7 |
| Pseudomonas sp. ATCC 21439 (Obligate) | 7.4 | 4.7 | 0.05 | 0.03 |
| Methanomonas methylovora ATCC 21852 (Obligate) | 0.28 | 2.5 | 2.1 | 1.0 |

[a]The products were identified by gas chromatography retention time comparisons with authentic standards. Analysis also revealed that no further conversion of the products occurred.
[b]The dry weight of the cells was about 0.2 g/100 ml culture broth.

EXAMPLE 5

Microbiological Conversion of Secondary Alcohols to Ketones

In this example, microbial cells of both methane- and methanol-utilizing methylotrophic microorganisms (both obligate and facultative types) were used to convert secondary alcohols to methyl ketones.

The procedure in Example 1 was repeated except that the methylotrophic microorganisms were each aerobically grown in an alcohol dehydrogenase-inducing growth medium containing methylamine or methyl formate as the alcohol dehydrogenase enzyme inducer and growth substrate instead of methane. The nutrients in the medium were the same as indicated in Example 1 except that 0.4% V/V of the alcohol dehydrogenase-inducer growth substrate was used as the major carbon and energy source. The cells were harvested and washed as described in Example 1. The resting microbial cells were then contacted with C$_3$–C$_6$ secondary alcohols in a buffered solution by the conversion procedure of Example 1. Table V shows the conversion rates of the secondary alcohols to the ketones for the methylamine-grown microbial cell suspensions and Table VI shows the conversion rates for the secondary alcohols to the ketones for the methyl formate-grown microbial cell suspensions.

experiments using the resting methane-, methanol-, methylamine- or methyl formate-grown microbial cells, the conversion reaction proceeded linearly for at least 4 hours.

The oxidative and/or alcohol dehydrogenase enzyme system of the aerobically induced methylotrophic mi-

TABLE V

Conversion Rates For Conversion of Sec-Alcohols to Ketone by Cell-Suspensions of Methylamine-Grown Obligate and Facultative Methanol-Utilizing Methylotrophs

| Methylotrophic Microorganism Strain Identification[b] | Conversion Rates[a] $\mu$moles/hr/mg protein | | | |
|---|---|---|---|---|
| | 2-Propanol to Acetone | 2-Butanol to 2-Butanone | 2-Pentanol to 2-Pentanone | 2-Hexanol to 2-Hexanone |
| Methanomonas methylovora ATCC 21852 (Obligate) | 0.82 | 3.2 | 1.0 | 0.09 |
| Pseudomonas sp. ATCC 21438 (Facultative) | 1.0 | 2.1 | 0.82 | 0.07 |

[a]The products were identified by gas chromatography retention time comparisons with authentic standards. Analysis also revealed that no further conversion of the products occurred.
[b]The dry weight of the cells was about 0.2 g/100 ml culture broth.

TABLE VI

Conversion Rates For Conversion of Sec-Alcohols to Ketones by Cell-Suspensions of Methyl Formate-Grown Obligate and Facultative Methane- and Methanol-Utilizing Methylotrophs

| Methylotrophic Microorganism Strain Identification[b] | Conversion Rates[a] $\mu$moles/hr/mg protein | | | |
|---|---|---|---|---|
| | 2-Propanol to Acetone | 2-Butanol to 2-Butanone | 2-Pentanol to 2-Pentanone | 2-Hexanol to 2-Hexanone |
| Methylosinus trichosporium OB3b NRRL B-11,196 (Obligate Methane-Utilizer) | 0.95 | 4.5 | 1.5 | 0.72 |
| Methylobacterium organophilum XX ATCC 27886 (Facultative Methane Utilizer) | 0.48 | 3.5 | 1.0 | 0.70 |
| Methanomonas methylovora ATCC 21852 (Obligate Methanol-Utilizer) | 0.62 | 2.1 | 1.5 | 0.60 |
| Pseudomonas sp. ATCC 21438 (Facultative Methanol-Utilizer) | 0.52 | 3.2 | 2.0 | 0.80 |

[a]The products were identified by gas chromatography retention time comparisons with authentic standards. Analysis also revealed that no further conversion of the products occurred.
[b]The dry weight of the cells was about 0.2 g/100 ml culture broth.

As shown above, a method has been discovered whereby methyl ketones are obtained by contacting $C_3$–$C_6$ n-alkanes or $C_3$–$C_6$ linear secondary alcohols with resting microbial cells (or enzyme preparations derived therefrom) which have been grown in the presence of an oxygenase and/or alcohol dehydrogenase enzyme inducer as the major carbon and energy source. The methylotrophic microorganisms may be either obligate or facultative. In either case, when the methylotrophic microorganisms are aerobically grown in a nutrient medium containing the enzyme inducer, methane, the resulting resting microbial cells or their enzyme preparations are capable of converting either the $C_3$–$C_6$ alkanes or $C_3$–$C_6$ secondary alcohols to the corresponding methyl ketones. In the case of either the obligate or facultative methylotrophic microorganisms which have been aerobically grown in a nutrient medium containing methanol, methylamine or methyl formate as the alcohol dehydrogenase enzyme inducer the resulting resting microbial cells or their enzyme preparations are only capable of converting $C_3$–$C_6$ secondary alcohols to the corresponding methyl ketones. These induced enzymes are not capable of converting the $C_3$–$C_6$ alkanes to the corresponding methyl ketones. In either case, no further reaction of the ketone product was detected. In batch croorganisms is inducible and the ketone product accumulates extracellularly (i.e., after the reaction takes place, and the reaction mixture is centrifuged, the ketone product is found in the supernatant fraction and not in the cell pellet.

It was found that some of the strains of methylotrophic microorganisms produce cells or enzyme preparations having a higher capability of converting secondary alcohols to ketones than others. For example, microbial cells derived from Methylosinus trichosporium OB3b produced the largest amount of methyl ketones from secondary alcohols (e.g., 15 $\mu$moles/2 mg. of protein after 2 hours).

As will be shown by the examples that follow, the methane-grown microbial cells and their enzyme preparations (including cell-free extracts) possess both oxygenase and alcohol dehydrogenase enzyme activity. It is believed that the methane itself induces the oxygenase enzyme activity and the methanol resulting from the oxidation of methane by the methylotrophic microorganism during growth induces the alcohol dehydrogenase enzyme. The induced oxygenase enzyme is responsible for converting the $C_3$–$C_6$ alkane to an intermediate oxidation product, the secondary alcohol, whereas the induced alcohol dehydrogenase enzyme dehydrogenates the secondary alcohol to the corresponding methyl ketone.

Also as shown in the examples that follow, in addition to methylotrophic bacteria, other microorganisms may be used to carry out the conversion of the $C_3$–$C_6$ alkanes or conversion of the $C_3$–$C_6$ secondary alcohols to the corresponding methyl ketones. These include bacteria, fungi and yeast which grow on short chain alkanes, e.g., methane or alcohols such as methanol, etc.

ALCOHOL OXIDATION SYSTEMS

As shown and discussed above (Tables II & III) resting-cell suspensions of methane- and methanol-grown microbial cells oxidized (dehydrogenated) $C_3$–$C_6$ secondary alcohols to their corresponding methyl ketones. The product methyl ketones accumulated extracellularly as determined by analysis of the supernatant of the centrifuged reaction mixture. Control experiments with heat-killed cells indicated that the methyl ketones were produced enzymatically. In these tests, secondary alcohol dehydrogenase (SADH) activity was found in all of the $C_1$-utilizers tested. Further tests have shown that SADH activity was found in cell suspensions of methanol-grown or methylamine-grown microorganisms. However, the SADH does not appear to be a constitutive enzyme since the SADH enzyme activity was not found in succinate-grown facultative $C_1$-utilizers.

To prepare the cell-free secondary alcohol dehydrogenase (SADH) system, the washed cells were disrupted with a Wave Energy Ultrasonic Oscillator, Model W201 (Wave Energy System, Inc., Newtown, Pa.) and centrifuged at $20,000 \times g$. for 30 minutes. The clear supernatant contained the SADH activity. The enzyme activity was measured with a fluorescence spectrophotometer (Perkin Elmer, Model MPF 44A) by following the formation of reduced NAD (EX 340 nm, Em 460 nm). The formation of reduced NAD was also followed with an absorption spectrophotometer at 340 nm. The assay system (3 ml.) contained: potassium phosphate buffer pH 7.0; 150 $\mu$mol.; NAD 1 $\mu$mol.; a given amount of enzyme preparation; and secondary alcohol 10 $\mu$mol. The reaction was started by the addition of substrate. One unit of enzyme activity represents the reduction of one $\mu$mole NAD per minute. Protein concentrations were determined by the Lowry method (*J. Biol. Chem.*, 193: 255–275 (1951)).

The following summarizes tests conducted on the optimal conditions for the production of methyl ketones from $C_3$–$C_6$ sec. alcohols. It will be understood that these were the optimal conditions found and the invention is not meant to be bound by them. Conversions can still be obtained by deviating from optimum indicated below, but with lower yields and conversions.

Time Course

The production of 2-butanone from 2-butanol reached a maximum after 14 hours of incubation in batch experiments in all the microorganisms tested. The amount of 2-butanone did not decline after 30 hours of incubation. The rate of 2-butanone production was linear for the first 4 hours. Therefore, the production of 2-butanone was measured within this interval whenever the effect of a variable was tested.

pH

The effect of pH on the production of 2-butanone was studied with tris (hydroxymethyl) amino methane-HCl buffer (0.05 M) for pH values of 8.0 to 10.0, and 0.05 M potassium phosphate buffer for values from 5.0 to 8.0. A pH around 8.0 was found to be the optimum for 2-butanone formation in all the microorganisms tested. Of the new strains, *Methylobacterium organophilum* CRL 26 (NRRL B-11,222), showed high activity at both 8 and 9. The yeast cells appeared less affected by pH in the production of 2-butanone.

Temperature

The temperature optimum for the production of 2-butanone by cell-suspensions was about 35° C. except for the yeast culture, which had an optimum of about 40° C.

Substrate Concentration

Various concentrations of 2-butanol were added to cell-suspensions of yeast and of strain *Pseudomonas sp.* ATCC 21,439. The production of 2-butanone was assayed after 35 min. of incubation. The amount of 2-butanone produced was dependent on the amount of substrate initially added. A 2-butanol concentration of about 50 $\mu$moles supported maximum 2-butanone production.

Cell Concentration

The cell concentration also has an influence on the rate of 2-butanone production. The amount of 2-butanone accumulated after 2 hours of incubation increased linearly as the cell concentration was increased up to about 12 mg./0.5 ml. for yeast and for *Methylococcus capsulatus* CRL M1 (NRRL B-11,219) and about 17 mg./0.5 ml. for strains *Methylobacterium organophilum* CRL 26 (NRRL B-11,222), *Methylosinus trichosporium* OB3b (NRRL B-11,196) and *Pseudomonas sp.* ATCC 21,439.

Product Inhibition and Further Oxidation

Examination of the time course of 2-butanone production revealed that the rate decreased after 4 hours of incubation, suggesting, among other possibilities, either product inhibition or further oxidation of 2-butanone. To test these possibilities, 8 $\mu$moles of 2-butanone was added to viable or heat-killed cell suspensions and incubated under the conditions described above for producing the 2-butanone. No decline was observed in 2-butanone concentration in all the heat-killed cell suspensions, but 2-butanone slowly disappeared in the presence of viable cells of all the strains tested. When 2-butanol (5 $\mu$l/0.5 ml. reaction mixture) was added to viable cell-suspensions along with the exogenously supplied 2-butanone, a net increase in 2-butanone production was detected. The reaction rates were identical to those where the secondary alcohol was initially converted to the methyl ketone and were not affected by the presence of the exogenously supplied 2-butanone. These data indicate that there is no product inhibition in the production of 2-butanone. A small amount of further oxidation of 2-butanone by viable cell-suspensions was observed. The decrease in 2-butanone production rate after 4 hours of incubation may be due to the depletion of other requirement(s), e.g., a cofactor(s).

Inhibition Studies

The production of 2-butanone from 2-butanol by cell suspensions of the strains tested was inhibited by metal-chelating agents such as 1, 10-phenanthroline and $\alpha,\alpha$-dipyridyl. However, the activity was not inhibited by sodium cyanide or thiourea which suggests metal involvement for the enzyme. The results of the inhibition tests are shown in Table VII.

TABLE VII

EFFECT OF METAL-CHELATING AGENTS AND OTHER INHIBITORS ON THE PRODUCTION OF 2-BUTANONE BY CELL SUSPENSIONS OF METHANOL-GROWN *METHYLOCOCCUS CAPSULATUS* CRL M1 (NRRL B-11,219)

| Metal-Chelating Agents | Concentration | Inhibition (%) |
|---|---|---|
| Sodium cyanide | 1 mM | 0 |
| Sodium azide | 1 mM | 10 |
| EDTA | 1 mM | 70 |
| 1,10-phananthroline | 1 mM | 95 |
| α, α-bipyridyl | 1 mM | 75 |
| Thiourea | 1 mM | 0 |

Substrate Specificity

The substrate specificity for the oxidation of $C_3$–$C_6$ secondary alcohols by the strains of $C_1$-utilizers was studied. Among the secondary alcohols, 2-propanol and 2-butanol were oxidized at higher rates; 2-pentanol, 2-hexanol, and 2-heptanol were oxidized at a much slower rate. The oxidation products of these secondary alcohols were the corresponding methyl ketones, as determined by GC retention time comparisons with authentic standards.

Cell-Free System

Cell-free soluble extracts from sonically disrupted cells of new strains and known strains also oxidized 2-butanol to 2-butanone. These results are shown in Table XVII. However, all of the cell-free systems tested required the addition of a cofactor, NAD, for its activity. Other cofactors, tested (including NAD(P)H, NADP, phenazine methosulfate, GSH, FAD, potassium ferricyanide, and dichlorophenol indophenol) were not effective. The stoichiometry for the consumption of 2-butanol, the reduction of NAD, and the formation of 2-butanone was obtained for *Pseudomonas sp.* ATCC 21,439 as shown in Table IX. This is the first report of an NAD-dependent secondary alcohol dehydrogenase.

The experimental procedure for the tests reported in Table VIII were as follows: 1 mg protein of crude extract was added into a 0.5 ml. 0.05 M phosphate buffer (pH 7.0) in a 10-ml. vial. One μmol NAD and 10 μmol 2-butanol was added, and the vial was sealed with a rubber cap to minimize evaporation. The reaction mixture was incubated at 30° C. on a water bath. A 3 μl sample was removed with a syringe at 15 min. of incubation and was assayed with g.l.c. Catalytic activity was also assayed by fluorescence spectrophotometry. Data obtained from both g.l.c. and fluorescence spectrophotometric assays agreed with each other. Comparable conversions (as reported in Table VIII) for extracts derived from $CH_3NH_2$ and $HCOOCH_3$ grown microbes were also obtained as shown in Table VIII. Table VIIIa similarly shows conversions of 2-propanol, 2-butanol and 2-pentanol to the methyl ketones with the cell-free extracts of SADH.

TABLE VIII

OXIDATION OF 2-BUTANOL TO 2-BUTANONE BY CELL-FREE SOLUBLE EXTRACTS of $C_1$-UTILIZING MICROBES[a]

| Microbes | Growth Substrate | Conversion Rate (nmoles/ min/mg protein) |
|---|---|---|
| Obligate methylotrophs | | |
| Type I membrane structure | | |
| *Methylosinus trichosporium* OB3b (NRRL B-11,196) | $CH_4$ | 4.5 |
| *Methylosinus trichosporium* OB3b (NRRL B-11,196) | $CH_3OH$ | 2.4 |
| *Methylosinus trichosporium* OB3b (NRRL B-11,196) | $CH_3NH_2$ | 2.5 |
| *Methylosinus trichosporium* OB3b (NRRL B-11,196) | $HCOOCH_3$ | 2.0 |
| *Methylosinus sporium* 5 (NRRL B-11,197) | $CH_4$ | 1.5 |
| *Methylocystis parvus* OBBP (NRRL B-11,198) | $CH_4$ | 1.2 |
| Type II membrane structure | | |
| *Methylomonas methanica* $S_1$ (NRRL B-11,199) | $CH_4$ | 0.5 |
| *Methylomonas albus* BG 8 | $CH_4$ | 2.5 |
| *Methylomonas streptobacterium* CRL 17 (NRRL B-11,208) | $CH_4$ | 1.8 |
| *Methylomonas agile* CRL 22 (NRRL B-11,209) | $CH_4$ | 1.4 |
| *Methylococcus capsulatus* CRL M1 (NRRL B-11,219) | $CH_4$ | 3.2 |
| *Methylococcus capsulatus* CRL M1 (NRRL B-11,219) | $CH_3OH$ | 2.0 |
| *Methylococcus capsulatus* CRL M1 (NRRL B-11,219) | $CH_3NH_2$ | 1.8 |
| *Methylococcus capsulatus* CRL M1 (NRRL B-11,219) | $HCOOCH_3$ | 2.0 |
| *Methylococcus capsulatus* Y (NRRL B-11,201) | $CH_4$ | 0.8 |
| Facultative methane-utilizers | | |
| *Methylobacterium organophilum* CRL 26 (NRRL B-11,222) | $CH_4$ | 1.8 |
| *Methylobacterium organophilum* CRL 26 (NRRL B-11,222) | $CH_3OH$ | 2.5 |
| *Methylobacterium organophilum* CRL 26 (NRRL B-11,222) | $CH_3NH_2$ | 2.0 |
| *Methylobacterium organophilum* CRL 26 (NRRL B-11,222) | $HCOOCH_3$ | 2.0 |
| *Methylobacterium organophilum* XX (ATCC 27,886) | $CH_4$ | 2.6 |
| Obligate methanol-utilizer | | |
| *Pseudomonas sp.* CRL 75 (ATCC 21,439) | $CH_3OH$ | 25.0 |
| *Methylomonas methylovora* (ATCC 21,852) | $CH_3OH$ | 2.0 |
| Facultative methanol-utilizers | | |
| *Pseudomonas sp.* CRL 74 (ATCC 21,438) | $CH_3OH$ | 3.0 |
| *Pseudomonas Ms.* (ATCC 25,262) | $CH_3OH$ | 5.0 |
| Yeasts | | |
| *Candida utilis* (ATCC 26,387) | $CH_3OH$ | 2.4 |
| *Candida utilis* (NRRL Y-660) | $CH_3OH$ | 15.0 |
| *Hansenula polymorpha* (ATCC 26,012) | $CH_3OH$ | 23.2 |
| *Hansenula polymorpha* (ATCC 26,012) | $CH_3NH_2$ | 20.0 |
| *Hansenula polymorpha* (ATCC 26,012) | $HCOOCH_3$ | 16.0 |
| *Hansenula polymorpha* (NRRL Y-2214) | $CH_3OH$ | 1.5 |
| *Hansenula polymorpha* (NRRL Y-2267) | $CH_3OH$ | 2.0 |
| *Hansenula anomala* (NRRL Y-336) | $CH_3OH$ | 1.8 |
| *Pichia pastoris* (NRRL Y-55) | $CH_3OH$ | 2.2 |
| *Pichia pastoris* | $CH_3OH$ | 1.6 |

TABLE VIII-continued
OXIDATION OF 2-BUTANOL TO 2-BUTANONE BY CELL-FREE SOLUBLE EXTRACTS of C$_1$-UTILIZING MICROBES[a]

| Microbes | Growth Substrate | Conversion Rate (nmoles/min/mg protein) |
|---|---|---|
| (NRRL Y-7556) | | |

[a]Cells were disrupted as described above and the supernatant of 10,000 x g. centrifugation was used for the enzyme assay.

TABLE VIIIa
OXIDATION OF SECONDARY ALCOHOLS BY SOLUBLE CRUDE EXTRACTS OF C$_1$-UTILIZERS GROWN ON METHANOL

| | Oxidation Rate (nmole/min/mg protein) | | | |
|---|---|---|---|---|
| C$_1$-Utilizer Microorganisms | 2-Propanol to Acetone | 2-Butanol to 2-Butanone | 2-Pentanol to 2-Pentanone | 2-Hexanol to 2-Hexanone |
| *Methylosinus trichosporium* OB3b (NRRL B-11,196) | 2.0 | 2.4 | 0.1 | 0 |
| *Methylococcus capsulatus* CRL M1 (NRRL B-11,219) | 1.7 | 2.0 | 0.1 | 0 |
| *Methylobacterium organophilum* CRL 26 (NRRL B-11,222) | 2.1 | 2.5 | 0.1 | 0 |
| *Pseudomonas sp.* (ATCC 21,439) | 21.2 | 25.0 | 1.2 | 0 |

TABLE IX
STOICHIOMETRY OF THE PRODUCTION OF 2-BUTANONE FROM 2-BUTANOL BY CELL-FREE EXTRACTS OF STRAIN ATCC 21439

| Experiment | 2-Butanol Consumed (nmoles) | NAD Consumed[b] (nmole) | 2-Butanone[a] Produced (nmole) |
|---|---|---|---|
| 1 | 260 | 270 | 250 |
| 2 | 530 | 540 | 520 |

The reaction mixtures 3 ml (1.0 mg protein) were incubated at 30° C. for 10 min. (exp. 1) and for 20 min. (exp. 2) in the presence of 1.0 μmoles NAD and 10 μmoles 2-butanol.
[a]Determined gas chromatographically.
[b]Determined fluorescence spectrophotometrically. Endogenous consumption of NAD was corrected.

Purification and Properties of Secondary Alcohol Dehydrogenase

Secondary alcohol dehydrogenase (SADH) from an obligate methanol utilizer, *Pseudomonas sp. ATCC* 21439 was purified as follows. The cells which has been grown on methanol as the carbon source as described in the preceding examples were suspended in 300 ml. 0.05 M sodium phosphate buffer, pH 7.0 with 0.5 mM dithiothretol (buffer A) and were disrupted sonically (5×1 min.). The crude extract was separated by centrifugation. The crude extract was heat-treated at 50° C. in a water bath for 10 minutes. The resulting precipitate was removed by centrifugation. To the supernatant solution, 25 ml of protamine sulfate solution (2% solution in 0.1 M Tris base) was added dropwise with continuous stirring. After standing for 30 minutes, the extract was centrifuged. The supernatant solution was fractionated with solid ammonium sulfate. The material prcipitating between 30 and 60% saturation was collected and was dialized overnight against buffer A. The dialized material was applied to a DEAE-cellulose column (3 cm by 35 cm) that had been equilibrated with buffer A. The secondary alcohol dehydrogenase activity was eluted in the void volume. This DEAE-cellulose eluate was concentrated by ammonium sulfate fractionation. Material precipitating between 30 and 50% ammonium sulfate saturation was collected by centrifugation and dialyzed overnight against A. This fraction was further washed and filtered through an Amicon unit with XM 50 membrane. The concentrated fraction (6 ml) inside the Amicon unit was applied to an Affi-Gel Blue column (0.8 cm × 18 cm) which had been equilibrated with buffer A for affinity chromatography. The column was washed overnight with buffer A (0.18 ml./min.) and then was eluted with buffer A containing 5 mM NAD. Each 1 ml. fraction was collected. SADH activity was located in tube numbers 8-12. A summary of the purification steps is shown in Table X.

TABLE X
PURIFICATION OF SECONDARY ALCOHOL DEHYDROGENASE FROM *PSEUDOMONAS SP.* ATCC 21439

| Procedures | Volume (ml) | Protein (mg) | Sp. Act. (units/mg protein) | Total units | Yield (%) |
|---|---|---|---|---|---|
| Crude extract | 250 | 2698 | 25 | 67450 | 100 |
| Heat treatment | 245 | 949 | 67.5 | 64080 | 95 |
| Protamine sulfate | 260 | 526 | 103.8 | 54640 | 81 |
| (NH$_4$)$_2$SO$_4$ (30–60% sat.) | 30 | 232 | 200 | 46450 | 69 |
| DEAE-cellulose column | 150 | 42.2 | 875 | 37160 | 55 |
| Amicon filtration (XM-50) | 6 | 22.0 | 1,500 | 33050 | 49 |
| Affi-Gel Blue column | 5 | 0.34 | 65,600 | 22300 | 33 |

The purified secondary alcohol dehydrogenase enzyme (SADH) may be used directly for converting C$_3$-C$_6$ secondary alcohols to the corresponding methyl ketones by the procedures described above; however, a source of NAD$^+$ must be added to the reaction medium. One can determine the NAD-linked secondary alcohol dehydrogenase activity with a fluorescence spectrophotometer (Perkin Elmer, Model MPF 44A) by following the formation of reduced NAD (Ex 340 nm, Em 460 nm). The assay system (3 ml.) will typically contain: sodium phosphate buffer pH 7.0, 150 μmol; NAD 1.0 μmol; a given amount of enzyme preparation; and 20 μmol secondary alcohol. The reaction is started by the addition of secondary alcohol. One unit of SADH enzyme activity represents the reduction of one nmole NAD per minute.

The purification procedure outlined in Table X may be modified by omitting the heat-treatment. A higher specific activity can be obtained by omitting the heat-treatment (a specific activity of 45 units of SADH/mg.

protein from *Pseudomonas sp.* ATCC 21,439 was obtained). The presence of a reducing agent such as dithrothretol in the dialyzing buffer was found essential during the dialysis of the material precipitated between 30–60% $(NH_4)_2SO_4$ saturation. In one specific experiment the Affi-Gel Blue column was scaled-up to a size of 2.5 cm×25 cm. From 10 liters of crude extract containing 200 g. protein, a 45 mg. pure SADH fraction with specific activity of 65,600 SADH units/mg. protein (33% recovery) was obtained.

Metal analysis of the purified SADH enzymes were conducted by x-ray fluorescence technique with a Phillips PW 1220C semi-automatic vacuum spectrograph. In carrying out the metal analysis the purified SADH was first washed thoroughly with deionized distilled water and then dried evenly on an Amicon XM 50 ultrafiltration membrane. This membrane was then assayed by x-ray fluorescence technique. Control experiments are taken with blank ultrafiltration membranes. The minimum amount of metal detectable qualitatively and quantitatively by this method are $>0.02$ μg. and $>0.5$ per $cm^2$, respectively. Metal analysis by this technique on the purified bacteria derived SADH enzymes showed 0.7 μg. zinc/$cm^2$ of the ultrafiltration membrane. This is equivalent to two moles of zinc per mole of SADH enzyme, or one zinc per subunit. No other metal was detected.

The molecular weight of the purified SADH was determined by acrylamide gel electrophoresis using 7.5% gel and stained with both coomassie brilliant blue and with nitro-blue tetrazolium activity stain. Sodium dodecyl sulfate-gel electrophoresis in a 10% gel system and the dissociation of enzyme protein was conducted using SDS-PAGE standards. Both the protein stain and the enzyme activity stain of the purified SADH enzymes tested showed a single protein band. The mobility on the gel electrophoresis of SADH from the distinct types of methanol-grown bacterial cells were identical. Yeast derived SADH has a faster mobility toward the anode on the gel electrophoresis. The molecular weights of several bacterial and yeast derived and purified SADH enzymes each had an identical molecular weight of 95,000 dalton as estimated by a Bio-Gel agarose A-1.5 column. SDS-gel electrophoresis of the purified enzymes showed to identical subunits of 48,000 dalton.

The optimum pH and temperatures for activity of the purified SADH was 8–9 and 30°–35° C., respectively, although wider ranges of pH and temperatures did not significantly affect the enzyme activity. The activation energy for SADH, as calculated from the Arrhenius plots of velocity vs. the reciprocal of the absolute temperature, is 19.8 K cal. The absorption spectrum of the purified SADH fraction showed no peak in the visible region.

The Michaelis constants ($K_m$) of SADH calculated from Line-Weaver-Burk plot was $1.1 \times 10^{-5}$ M for NAD. Similar reaction rates were obtained whether SADH was preincubated for 10 min. with either NAD or 2-butanol. This indicates that the addition of substrates in the SADH reaction is not an obligatory order and is rather a random mechanism. No consumption of dissolved oxygen was observed during the reaction.

The effect of metal-chelating agents and thioreagents on the activity of the purified SADH enzyme were studied. The SADH activity was inhibited as follows (% inhibition, activity measured spectrofluorometrically and each inhibitor added at a final concentration of 1 mM): iodoacetic acid, 0%; N-ethylmalemide, 6%; p-hydroxymercuribenzoate, 100%; 5,5'-dithiobis(2-nitrobenzoic acid), 100%; sodium cyanide, 0%; sodium azide, 10%; EDTA, 63%; 1,10-phenanthroline, 95%; α,α-bipyridyl, 70%; thiourea, 0%; cupric, 25%; ferric, 35%; ferrous, 50%; nickel, 20%; and $Zn^{++}$, $Co^{++}$, $Mn^{++}$, or $Mg^{++}$, 0%. Despite the fact that SADH contains 2 moles of zinc per mole of enzyme, the addition of exogenous zinc did not stimulate its activity. The possibility of ethanol or n-propanol as an inhibitor was studied. Despite their structural similarity in competing with 2-butanol for the alkyl binding site(s), both of them did not inhibit SADH activity.

The substrate specifically of purified SADH was highest for 2-propanol and 2-butanol. It also oxidized at a lower rate, 2-pentanol, 2-hexanol, acetaldehyde, propanol, cyclohexanol, butane 1,3-diol and butane 2,3-diol. Primary alcohols were not substrates of purified SADH. It appears that a hydrophobic carbon moiety adjacent to the secondary alcohol is required for enzyme activity.

The purified SADH enzyme was analyzed for amino acids with a Beckman Model 120B amino acid analyzer following acid hydrolysis of the enzyme. The results of the amino acid analysis are summarized in Table XI. The values are expressed as average number of residues per molecule obtained from 24, 48 and 72 hours acid hydrolysis, assuming a molecular weight of 95,000. Only two residues of cysteine ware detected.

TABLE XI

AMINO ACID COMPOSITION OF PURIFIED SADH[a]

| Amino Acid | No. of Residues/ 95,000 dalton |
|---|---|
| Lysine | 52 |
| Histidine | 14 |
| Arginine | 26 |
| Cysteic Acid | 2 |
| Aspartic Acid | 78 |
| Threonine | 26 |
| Serine | 14 |
| Glutamine | 76 |
| Proline | 32 |
| Glycine | 72 |
| Alanine | 92 |
| Valine | 68 |
| Methionine | 6 |
| Isoleucine | 54 |
| Leucine | 74 |
| Tyrosine | 6 |
| Phenylalanine | 28 |
| Tryptophane | 28 |

[a]The secondary alcohol dehydrogenase enzyme was purified from cells derived from *Pseudomonas sp.* ATCC 21,439 aerobically grown on methanol.

Yeast Derived SADH

As previously indicated both cell suspensions and cell-free extracts of $C_1$-compound grown yeasts enzymatically convert $C_3$–$C_6$ secondary alcohols to the corresponding methyl ketones. Further, we specifically found that cell suspensions of the yeasts: *Candida utilis* ATCC 26,387; *Hansenula polymorpha* ATCC 26,012 *Pichia sp.* NRLL Y-11,328; *Torulopsis sp.* strain $A_1$ NRRL Y-11,419; and *Kloeckera sp.* strain $A_2$ NRRL Y-11,420 grown on various $C_1$ compounds (e.g., methanol, methylamine, methyl formate), ethanol and propylamine catalyzed the oxidation of $C_3$–$C_6$ secondary alcohols to the corresponding methyl ketones.

The cells were harvested during exponential growth by centrifugation at 12,000×g. for 15 min. The cell pellet was washed twice with 50 mM phosphate buffer, pH 7. The final pellet was resuspended in the same buffer. Cell suspensions of yeasts grown on ethanol, methylamine, and methylformate were prepared as described above using 0.4 v/v ethanol, 10 mM methylamine and 10 mM methylformate as the sole source of carbon and energy.

A 1 ml. aliquot of each washed cell suspension of yeasts grown on various carbon sources was put into 10 ml. vials at 40° C. Ten μl of secondary alcohol (2-propanol, 2-butanol, 2-pentanol and 2-hexanol) was added to the cell suspensions in an independent vial. The vials were then incubated at 30° C. on a rotary water bath shaker at 200 rpm. The product of oxidation of secondary alcohols was detected by gas chromatography retention time comparison and co-chromatography with authentic standard. As shown in Table XII the cell suspensions of yeasts catalyze the conversion of isopropanol, 2-butanol, 2-pentanol, and 2-hexanol to the corresponding methyl ketones. The products of oxidation of secondary alcohols were accumulated extracellularly and no further oxidation of products (methyl ketones) was revealed by gas chromatographic analysis. Similar conversions of 2-butanol to 2-butanone were made with cell suspensions of the yeasts: *Candida boidinii* NRRL Y-2332; *Hansenula anomala* NRRL Y-336; and *Pichia pastoris* NRRL Y-55. The conversion rates (μ moles/hr/mg. protein) were 6.0, 5.5 and 5.8, respectively. $C_3$–$C_6$ secondary alcohols to the corresponding methyl ketones. Cell-free extracts of these yeasts catalyzed the $NAD^+$-dependent oxidation of the $C_3$–$C_6$ secondary alcohols to the corresponding methyl ketones. The presence of $NAD^+$ as an electron acceptor was essential in the case of the cell-free extract of these yeast derived enzymes. Primary alcohols were not oxidized by this purified enzyme. The molecular weight of the purified yeast derived SADH enzyme was 98,000 dalton as determined by gel filtration and the subunit size as determined by sodium dodecyl sulfate gel electrophoresis was 48,000.

It is to be noted that the molecular weight of the purified SADH whether yeast or bacteria derived is about 95,000, ±3000 (by Bio-gel column chromatography) but may vary due to purification procedures and experimental error.

The activity of the purified yeast derived SADH was inhibited by sulfhydryl inhibitors and metal-binding agents. The optimum pH of the purified enzyme was determined to be about 8.

A typical yeast derived SADH enzyme was prepared as follows:

The yeasts were grown at 30° C. in 2.8 liter flasks containing 700 ml. mineral salts medium (described below) with 0.1% yeast extracts and 0.4%, v/v methanol.

| Yeast Growth Medium[a] | |
|---|---|
| $KH_2PO_4$ | 2.5 gm. |
| $NH_4NO_3$ | 2.5 gm. |
| $MgSO_4 \cdot 7H_2O$ | 0.3 gm. |
| KCl | 0.04 gm. |
| $CaCl_2$ | 0.015 gm. |
| $FeSO_4 \cdot 7H_2O$ | 1.0 mg. |
| $CuSO_4 \cdot 5H_2O$ | 0.01 mg. |
| $H_3BO_3$ | 0.02 mg. |
| $MnSO_4 \cdot 5H_2O$ | 0.04 mg. |
| $ZnSO_4$ | 0.14 mg. |
| $MoO_3$ | 0.02 mg. |
| Yeast extract | 1.0 gm. |
| Methanol | 4 ml. |

[a] The following composition is on a per liter basis.

TABLE XII

OXIDATION OF SEC-ALCOHOLS TO KETONES BY CELL SUSPENSIONS OF YEASTS[a]

| Organism | Growth Substrate | Conversion Rate (μmoles/hr/mg of protein) | | | |
|---|---|---|---|---|---|
| | | Isopropanol to Acetone | 2-Butanol to 2-Butanone | 2-Pentanol to 2-Pentanone | 2-Hexanol to 2-Hexanone |
| *Candida utilis* ATCC 26387 | Methanol | 6.2 | 6.8 | 1.5 | 0.8 |
| | Ethanol | 5.2 | 5.2 | 1.0 | 0.72 |
| | Methylamine | 5.0 | 5.0 | 1.2 | 0.61 |
| | Methylformate | 5.6 | 6.2 | 1.3 | 0.75 |
| | Propylamine | 4.2 | 4.2 | 0.9 | 0.52 |
| *Hansenula polymorpha* ATCC 26012 | Methanol | 5.9 | 5.8 | 1.4 | 0.72 |
| | Ethanol | 5.0 | 4.8 | 1.1 | 0.54 |
| | Methylamine | 5.2 | 4.5 | 1.2 | 0.62 |
| | Methylformate | 5.6 | 5.2 | 1.3 | 0.70 |
| | Propylamine | 4.1 | 4.0 | 0.82 | 0.48 |
| *Pichia sp.* NRRL-Y-11328 | Methanol | 5.2 | 6.8 | 1.2 | 0.50 |
| | Ethanol | 4.5 | 6.2 | 1.0 | 0.28 |
| | Methylamine | 4.2 | 5.1 | 0.72 | 0.31 |
| | Methylformate | 4.9 | 6.9 | 0.98 | 0.48 |
| | Propylamine | 3.2 | 2.1 | 0.60 | 0.21 |
| *Torulopsis sp.* Strain $A_1$ (NRRLY-11,419) | Methanol | 4.5 | 4.9 | 1.0 | 0.21 |
| | Ethanol | 4.2 | 4.7 | 1.2 | 0.20 |
| | Methylamine | 4.3 | 4.5 | 0.9 | 0.12 |
| | Methylformate | 4.5 | 4.9 | 1.1 | 0.25 |
| | Propylamine | 3.2 | 3.8 | 0.62 | 0.10 |
| *Kloeckera sp.* Strain $A_2$ (NRRLY-11,420) | Methanol | 4.8 | 5.9 | 1.2 | 0.25 |
| | Ethanol | 4.5 | 5.7 | 1.0 | 0.12 |
| | Methylamine | 4.0 | 5.4 | 1.0 | 0.10 |
| | Methylformate | 4.9 | 5.9 | 1.2 | 0.28 |

TABLE XII-continued

OXIDATION OF SEC-ALCOHOLS TO KETONES BY CELL SUSPENSIONS OF YEASTS[a]

| Organism | Growth Substrate | Conversion Rate ($\mu$moles/hr/mg of protein) | | | |
|---|---|---|---|---|---|
| | | Isopropanol to Acetone | 2-Butanol to 2-Butanone | 2-Pentanol to 2-Pentanone | 2-Hexanol to 2-Hexanone |
| | Propylamine | 4.0 | 4.2 | 0.92 | 0.11 |

[a]The products of oxidation were identified by gas chromatography retention time comparison and co-chromatography with authentic standard. Analysis also revealed that no further oxidation of products (methylketones) occurred.

Cell suspensions (2 g. wet weight) of packed cells in 10 ml. of 50 mM sodium phosphate buffer, pH 7.0 at 4° C. were disrupted by sonication with a Megason ultrasonic disintegration. The sonicated cell suspensions were centrifuged for 15 minutes at 30,000×g. The supernantant liquid was termed the crude extracts.

Purification of Secondary Alcohol Dehydrogenase Derived from Yeast

Large scale cultures of *Pichia sp.* NRRL Y-11,328 were grown with aeration at 30° C. in a 14-liter New Brunswick f fermentor in a mineral salt medium containing methanol (0.4%, v/v) as the sole carbon source. The cells (200 g., wet weight) were suspended in 50 mm sodium phosphate buffer, pH 7.0, containing 1 mM dithiothreitol (buffer A), and crude extracts were prepared as described previously. To the crude extracts, 18 ml. of protamine sulfate solution [2% solution in 0.1 M tris (hydroxymethyl) aminomethane (tris) base] was added dropwise with continuous stirring. After standing for 30 min., the extracts were centrifuged at 20,000× g. for 60 min. The supernatant solution was fractionated with solid ammonium sulfate. Extracts were brought to 50% of saturation with respect to ammonium sulfate by addition of 313 g. of the salt per liter of extract. Precipitated proteins was removed by centrifugation, and 137 g. of ammonium sulfate was added per liter of the supernatant liquid to bring it to 70% of saturation. Material precipitating between 50 and 70% of saturation was collected by centrifugation and dissolved in buffer A. This preparation was dialyzed overnight against buffer A, and the dialyzed material was applied to a DEAE-cellulose column (5×40 cm) that had been equilibrated with buffer A. The sample was washed with 200 ml. of buffer A and eluted with 2 liters of buffer A that contained NaCl in a linear gradient running from a concentration of 0 to 0.5 M. Fractions of 15 ml. were collected. Fractions containing secondary alcohol dehydrogenase activity were pooled and were termed DEAE-cellulose eluate. The DEAE-cellulose eluate was concentrated by ammonium sulfate fractionation. Material precipitating between 50 and 70% of ammonium sulfate saturation was collected by centrifugation and dissolved in buffer A. This preparation was dialyzed overnight against buffer A, and 4 ml. samples were passed through a Bio-Gel agarose A1.5 column (2.5×100 cm) that had been equilibrated with buffer A. Fractions containing constant specific activity of enzyme were pooled and concentrated by Amicon ultrafiltration using an XM 50 filter.

The reaction mixture, in a total of 3.0 ml., contained 50 mM phosphate buffer, pH 7.0, 20 $\mu$mole NAD+, cell extracts (1 ml.). The reactions were started by the addition of 50 moles of secondary alcohol (isopropanol, 2-butanol, 2-pentanol, 2-hexanol) and the rate of production of methyl ketones (acetone, 2-butanone, 2-pentanone, 2-hexanone) was measured by gas chromatography.

The ketone product obtained from oxidation of sec-alcohols by cell extracts of organisms were estimated by flame ionization gas chromatography by using a stainless steel column (12 ft. by ⅛ in.) packed with 10% Carbowax 20 M on 80/100 chromosorb w column (Perkin Elmer Corp., Norwalk, Conn.). The column temperature was maintained isothermally at 130° C. and the carrier gas flow was 30 ml. of helium per min. The various ketone products (acetone, 2-butanone, 2-pentanone, 2-hexanone) were identified by retention time comparisons and co-chromatography with authentic standard. The protein content of cell-suspensions was determined by the Lowry et al. method.

Secondary alcohol dehydrogenase activity was measured spectrophotometrically at 340 nm with a NAD+ as an electron acceptor. The reaction mixture, in a total 3.0 ml., contained 50 mM phosphate buffer, pH 8.0, 5 $\mu$moles NAD+, crude extracts, and substrate. The reactions were started by addition of 100 $\mu$l of 0.1 M substrate and the rate of NAD+ reduction was measured. Protein concentration was determined by the method of Lowry et al.

Cell free extracts derived from yeasts, *Candida utilis* ATCC 26,387, *Hansenula polymorpha* ATCC 26,012, *Pichia sp.* NRRL Y-11,328, *Torulopsis sp.* strain A₁ NRRL Y-11,419 and *Kloeckera sp.* strain A₂ NRRL Y-11,420 grown on methanol catalyzed an NAD+-dependent oxidation of secondary alcohols (isopropanol, 2-butanol, 2-pentanol, 2-hexanol) to the corresponding methyl ketones (acetone, 2-butanone, 2-pentanone, 2-hexanone). The rate or production of methyl ketones from secondary alcohols are shown in Table XIII. Oxidation of secondary alcohols were also estimated spectrophotometrically by measuring the reduction of NAD+. The specific activities (nmoles NAD+ reduced per min. per mg. protein) of 78, 85, 105, 62, and 90 were obtained with extracts derived from *Candida utilis* ATCC 26,387*Hansenula polymorpha* ATCC 26,012, *Pichia sp.* NRRL Y-11,328 *Torulopsis sp.* NRRL Y-11,419 strain A₁ and *Kloeckera sp.* strain A₂ NRRL Y-11,420, respectively, using 2-butanol as a substrate.

TABLE XIII

OXIDATION OF SECONDARY ALCOHOLS TO METHYLKETONE BY CELL EXTRACTS OF YEASTS

| Organisms | Conversion Rate[a] $\mu$moles/hr/mg Protein | | | |
|---|---|---|---|---|
| | Isopropanol to Acetone | 2-Butanol to 2-Butanone | 2-Pentanol to 2-Pentanone | 2-Hexanol to 2-Hexanone |
| *Candida utilis* ATCC 26,387 | 4.5 | 4.92 | 0.82 | 0.45 |
| *Hansenula polymorpha* ATCC 26,012 | 4.8 | 5.2 | 1.0 | 0.51 |

TABLE XIII-continued
OXIDATION OF SECONDARY ALCOHOLS TO METHYLKETONE BY CELL EXTRACTS OF YEASTS
Conversion Rate[a]

| | μmoles/hr/mg Protein | | | |
|---|---|---|---|---|
| Organisms | Isopropanol to Acetone | 2-Butanol to 2-Butanone | 2-Pentanol to 2-Pentanone | 2-Hexanol to 2-Hexanone |
| Pichia sp. NRRL-Y-11,328 | 5.5 | 6.2 | 1.2 | 0.60 |
| Torulopsis sp. strain A₁ NRRL-Y-11,419 | 4.5 | 4.9 | 1.0 | 0.21 |
| Kloeckera sp. strain A₂ NRRL-Y-11,420 | 4.8 | 5.9 | 1.2 | 0.25 |

[a]Reactions were carried out as described above. The products of oxidation of secondary alcohols were identified and estimated by gas chromatography.

The SADH enzyme was eluted from a DEAE-cellulose column at 0.08 M NaCl concentration. The overall 60-fold purification was achieved from crude extracts. Purity of the enzyme preparation was examined by polyacrylamide gel electrophoresis. The purified enzyme preparations migrated as a single protein band when subjected to electrophoresis on polyacrylamide gel. Table XIV illustrates a summary of the purification steps and an analysis of the products at the end of each step.

The substrate specificity of the purified secondary alcohol dehydrogenase was examined spectrophotometrically. Among various secondary alcohls tested, the enzyme catalyzed the oxidation of isopropanol, 2-butanol, 2-pentanol, and 2-hexanol.

2-Heptanol, 2-octanol, methanol, ethanol, propan-1-ol, butan-1-ol, pentan-1-ol, 1,2-propandiol, 1,2-butandiol and 1,3-butandiol were not oxidized by the purified enzyme.

The purified enzyme required NAD+ as an electron acceptor. NADP, phenazine methosulfate, potassium ferricyanide, cytochrome c, 2,6-dichlorophenol indophenol, flavin adenine dinucleotide could not act as electron carrier.

Various primary alcohols not oxidized by secondary alcohol dehydrogenase were tested as potential inhibitors of enzyme activity. Enzyme activity was not inhibited by primary alcohols when tested at $10^{-3}$ M. Among various sulfhydryl inhibitors and metal-binding compounds tested, p-hydroxy mercaribenzoate, glutathione, imidiazole and 1,10 phenanthroline were strongly inhibited secondary alcohol dehydrogenase activity. Enzyme activity was also inhibited by heavy metals such as silver nitrate, mercuric thiocyanate and cupric sulfate.

TABLE XIV
PURIFICATION OF SECONDARY ALCOHOL DEHYDROGENASE FROM Pichia sp. NRRL Y-11,328[a]

| Step | Vol. (ml) | Protein (mg) | Units | Sp. activity (Units/mg. of Protein) | Yield % |
|---|---|---|---|---|---|
| 1. Crude extracts | 875 | 21,875 | 2391375 | 109 | 100 |
| 2. Protamine sulfate treatment | 890 | 21,360 | 2370960 | 111 | 99 |
| 3. Ammonium sulfate fractionation (50–70% saturation) | 117 | 3,090 | 1820010 | 589 | 76 |
| 4. DEAE-cellulose eluate | 55 | 200 | 706800 | 3534 | 29 |
| 5. Bio-Gel chromatography | 19 | 52 | 312624 | 6012 | 13 |

[a]Secondary alcohol dehydrogenase activity was estimated spectrophotometrically as described above using 2-butanol as a substrate. Specific activity was expressed as nanomoles of NAD+ reduced per min per mg of protein.

Acetone and 2-butanone was detected as the product of oxidation of isopropanol and 2-butanol, respectively, by the purified enzyme. The amount of NAD+ reuced and product formed is consistent with quantitative oxidation of both substrates. These results are shown in Table XV.

TABLE XV
STOICHIOMETRY OF ISOPROPANOL AND SEC-BUTANOL OXIDATION BY THE PURIFIED SECONDARY ALCOHOL DEHYDROGENASE

| Substrate (μmoles) | | NAD+ Reduced[a] (μmoles) | Product Formed[b] (μmoles) | |
|---|---|---|---|---|
| Isopropanol | 5.7 | 5.4 | Acetone | 5.5 |
| 2-Butanol | 6.0 | 5.9 | 2-Butanone | 5.7 |

[a]The estimation of NAD+ reduced was measured spectrophotometrically at 340 nm.
[b]The estimation of products was detected by gas chromatography as described in the methods.

ALKANE OXIDATION SYSTEM

Both cell suspensions (particulate fraction) and cell-free particulate fraction of methane-grown methylotroph microorganisms are capable of catalyzing the conversion of $C_3$-$C_6$ n-alkanes to the corresponding alcohols including secondary alcohols. The conditions for preparing the cell suspensions or the cell-free particulate fractions from methane-grown methylotroph microorganisms is the same as described above. The cell-free particulate fraction requires the presence of oxygen and NADH as an electron donor. The conversion to the alcohol was inhibited by metal-binding agents which suggests the involvement of metal ion(s) in the conversion of the alkanes to secondary alcohols. Propylene was also found to inhibit the conversion which suggests that the propylene and n-alkane (e.g., propane) are competing for the same enzyme system(s). Ascorbate and reduced nicotinamide adenine dinucleotide phosphate (NADPH) could also be utilized as an electron donor in place of NADH for the conversion. Tables XVI and XVII show the conversion of $C_3$-$C_6$ n-alkanes to the corresponding secondary alcohols using cell suspensions and cell-free particulate fractions, respectively, of methane-grown methylotroph microorganisms.

TABLE XVI
CONVERSION OF N-ALKANES TO SECONDARY ALCOHOLS BY MICROORGANISMS[a]

| Microorganisms | Growth Substrate | Conversion Rate μmoles/hr/$^5$mg. protein | | | |
|---|---|---|---|---|---|
| | | n-propane to 2-propanol | n-butane to 2-butanol | n-pentane to 2-pentanol | n-hexane to 2-hexanol |
| *Methylosinus trichosporium* (OB3b, NRRL-B-11,196) | Methane | 2.5 | 1.5 | 0.06 | 0.01 |
| *Methylococcus capsulatus* (Texas, ATCC 19,069) | Methane | 1.1 | 1.0 | 0.032 | 0.01 |
| *Methylobacter capsulatus* (Y, NRRL-B-11,201) | Methane | 0.20 | 0.09 | — | — |
| *Methylosinus sp.* (CRL-15, NRRL-B-11,202) | Methane | 2.1 | 1.2 | — | — |
| *Methylobacterium sp.* (CRL-26, NRRL-B-11,208) | Methane | 1.4 | 0.80 | 0.01 | 0.007 |
| *Methylomonas sp.* (CRL-17, NRRL-B-11,209) | Methane | 1.6 | 1.2 | — | — |

[a]The product secondary alcohols were identified and estimated by GC retention time comparison and co-chromatography with authentic standards.

TABLE XVII
HYDROXYLATION OF N-ALKANES TO SECONDARY ALCOHOLS BY PARTICULATE P(40)[a] FRACTION OF METHYLOTROPHS:

| Organisms | Conversion Rate μmoles/hr/2.0mg. of protein | |
|---|---|---|
| | n-propane to 2-propanol | n-butane to 2-butanol |
| *Methylosinus sp.* (CRL-15, NRRL-B-11,202) | 1.5 | 0.89 |
| *Methylococcus capsulatus* (Texas, ATCC 19,069) | 1.2 | 0.92 |
| *Methylosinus trichosporium* (OB3b, NRRL-B-11,196) | 1.32 | 0.79 |
| *Methylobacterium sp.* (CRL-26, NRRL-B-11,222) | 1.0 | 0.61 |

[a]Particulate P(40) fraction was prepared as follows: Cell-suspensions at 4° C. were disintegrated through a French Pressure cell and centrifuged at 4000 × g. for 15 min. to remove unbroken bacteria. The supernatant solution was then centrifuged at 40,000 × g. for 30 min. at 4° C., yielding the particulate P(40) and soluble S(40) fractions. The products were identified by gas chromatography and co-chromatography with authentic standard.

Table XVIII shows that cell suspensions of methane-grown methylotroph microorganisms convert $C_1$-$C_2$ alkanes to the corresponding alcohols and propane and butane are converted to a plurality of oxidation products, including primary and secondary alcohols, methyl ketones and aldehydes.

TABLE XVIII
CONVERSION OF n-ALKANES To OXIDATION PRODUCTS[a]

| Substrate | Products | Conversion Rate μmoles/hr./mg./protein | |
|---|---|---|---|
| | | *Methylosinus trichosporium* OB3b NRRL B-11,196 | *Methylococcus capsulatus* CRL M1 NRRL B-11,219 |
| Methane | Methanol | 1.5 | 2.5 |
| Ethane | Ethanol | 1.3 | 2.0 |
| Propane | 1-Propanol | 0.4 | 0.5 |
| Propane | 2-Propanol | 0.6 | 0.7 |
| Propane | Propanol | 0.1 | 0.2 |
| Propane | Acetone | 0.2 | 0.3 |
| Butane | 1-Butanol | 0.3 | 0.4 |
| Butane | 2-Butanol | 0.4 | 0.5 |
| Butane | 2-Butanone | 0.1 | 0.2 |
| Butane | n-butanol | 0.1 | 0.2 |

[a]Cell-suspensions of methane-grown methylotroph microorganisms indicated in 0.15 M phosphate buffer, pH 7.0 incubated in the alkanes as indicated at 3° C. The oxidation products were determined by g.l.c.

SUMMARY

Leadbetter and Foster (*Archiv. fur Mikrobiologie*, 35: 92–104 (1960)) reported tht methane grown *Pseudomonas methanica* co-oxidized propane and butane to their corresponding methyl ketones. They stated that resting cell-suspensions of methane-grown cells, however, did not oxidize propane or butane. Later, Lukins and Foster (*J. Bacteriol.*, 85: 1074–1086 (1963)) reported that propane-grown *Mycobacterium smegmatis* 422 oxidized n-alkanes to their corresponding methyl ketones. We have found and demonstrated that resting cell-suspensions of methane-grown cells oxidize $C_3$-$C_6$ alkanes to their corresponding secondary alcohols and methyl ketones in the absence of growth substrates. In addition, we have demonstrated for the first time the conversion of $C_3$-$C_6$ secondary alcohols to their corresponding methyl ketones by resting cell suspensions (particulate fraction) of either alkane-grown on alcohol grown cells. Succinate-grown cells do not have SADH activity, suggesting that either alkane or alcohol is required for inducing the enzyme.

As shown above, cell suspensions of these new cultures as well as known $C_1$-utilizers grown on either methane or methanol oxidized secondary alcohols to their corresponding methyl ketones. The cultures tested were selected from distinct general and they were compared for their optimal conditions in the production of 2-butanone. These cultures were: *Methylosinus trichosporium* OB3b (NRRL B-11,196) (a Type I obligate methane-utilizer); *Methylobacterium organophilum* CRL 26 (NRRL B-11,222) (a facultative methane-utilizer); *Hansenula polymorpha* ATCC 26012; and *Pseudomonas sp.* ATCC 21439 (an obligate methanol-utilizer). The rate of 2-butanone production was linear for the first 4 hours of incubation for all five cultures tested. The yeast culture had the highest production rate. The optimum temperature for the production of 2-butanone was 35° C. for all the bacteria tested. The yeast culture had a higher temperature optimum (40° C.), and a reasonably high 2-butanone production rate was also observed at 45° C. for this yeast. The production of 2-butanone was affected by substrate concentration and cell concentration. The inhibition by metal-chelating agents of the production of 2-butanone suggests the involvement of metal(s). No product (2-butanone) inhibition was observed in any of the cell-suspensions from all the five cultures tested.

We have found that cell-free soluble extracts from sonically disrupted cells also oxidize 2-butanol to 2-butanone. The cell-free system requires addition of a cofactor, specifically NAD, for its activity. One of the explanations for the rate decreases in 2-butanone production after 4 hours of incubation, therefore, may be the depletion of NAD in the cell suspensions.

Nicotinamide adenine dinucleotide (NAD) was found to be a requirement for the oxidation of $C_3$-$C_6$ secondary alcohols in the cell-free SADH system. Other co-factors tested (including PMS, GSH, FAD, potassium ferricyanide, dichlorophenol indophenol, and NADP) were not effective.

The molecular weight of the pure SADH as estimated by a Bio-Gel agarose A-1.5 column is 95,000 dalton. Acrylamide gel electrophoresis of the purified SADH fraction from the affinity chromatography showed a single protein band. The Km values for 2-butanol and NAD are 0.25 mM and 0.011 mM, respectively. The pH optimum for SADH activity was around 8–9 (0.05 M sodium phosphate buffer for pH 5 to 8; 0.05 M sodium pyrophosphate buffer for pH 8 to 11).

SADH oxidizes $C_3$-$C_6$ secondary alcohols with the following relative percent rate: 2-propanol (85%), 2-butanol (100%), 2-pentanol (5%), 2-hexanol (2%), acetaldehyde (4%), ropanal (2%), cyclohexanol (4%), butane 1,3-diol (2%), and butane 2,3-diol (;b 2.5%). The following compounds tested were not oxidized by SADH: 2-heptanol to 2-decanol, formaldehyde, butanal to decanal, benzaldehyde, methanol to n-decanol, isobutanol, phenol, butane 1,2-diol, and succinic acid. It seems that a hydrophobic carbon moiety adjacent to the secondary alcohol is required for the enzyme activity.

The SADH activity was inhibited by metal-chelating agents in the following order (percent inhibition): 1,10-phenanthroline (95%), α,α-bipyridyl (70%), EDTA (63%), and sodium azide (10%). This suggests possible metal involvement. However, the activity was not inhibited by sodium cyanide or thiourea. The enzyme activity was also inhibited by strong thio inhibitors such as p-hydroxy mercuribenzoate (100%) and 5,5'-dithiobis (2-nitrobenzoic acid) and was not inhibited by less potent thio inhibitors such as iodoacetic acid or N-ethylmaleimide. The physiological significance of this SADH is methylotrophs as well as other gaseous hydrocarbon utilizers is not known. However, possessing this enzyme is of great advantage to the organism as its growth yield, when growing on gaseous alkanes as the sole source of carbon and energy, could be exclusively NAD(P)H-dependent. Secondary alcohols are intermediates in the oxidation of n-alkanes by either Pseudomonas or Mycobacterium. The methane monooxygenase from *Methylococcus capsulatus* (Bath) also oxidizes n-alkanes to both primary and secondary alcohols. The fact that SADH is also present in the methanol-grown cells indicates that the enzyme is not induced by n-alkanes.

The metabolism of the obligate methylotrophs is uniquely dependent on a one-carbon compound (formaldehyde) for the biosynthesis of certain essential cellular constituents. This compound can be obtained from methane and methanol, but is unobtainable from the non-growth-supporting compounds.

NAD-dependent alcohol dehydrogenase and PMS-dependent methanol dehydrogenase are well characterized enzymes. Both of these dehydrogenases have a broad specificity toward primary alcohols. Recently, Metha (*J. Bacteriol.*, 124: 1165–1167 (1975)) reported an NAD-linked alcohol dehydrogenase from a yeast grown on methanol. This primary alcohol dehydrogenase also oxidizes 2-propanol. In addition, the report stated that this alcohol dehydrogenase was very unstable that it lost all of its enzyme activity within 24 hours after fourfold purification. Results from our preliminary studies, however, indicate that our secondary alcohol dehydrogenase is a secondary alcohol-specific enzyme with highest activity on 2-propanol and 2-butanol, and has no activity towards primary alcohols.

What is claimed is:

1. A process for the microbiological conversion of a $C_3$-$C_6$ liner secondary alcohol to the corresponding methyl ketone comprising oxidizing said alcohol by contacting a $C_3$-$C_6$ linear secondary alcohol, under aerobic conditions, with microbial cell derived from a methylotrophic microorganism or an enzyme preparation derived from said microorganism, wherein said secondary alcohol is converted to the corresponding methyl ketone by said cells or enzyme preparation, wherein said microorganism has been previously grown under aerobic conditions in a nutrient medium containing a carbon-containing compound which provides the carbon and energy source for growth of the cells of the microorganism and induces $C_3$-$C_6$ secondary alcohol dehydrogenase enzyme activity in said cells and wherein said methyl ketone is produced in insolable amounts.

2. The process of claim 1 wherein said microbial cells are derived from either a methane-utilizing or methanol-utilizing type methylotrophic microorganism.

3. The process of claim 2 wherein said methylotrophic microorganism is either obligate or facultative.

4. The process of claim 1 wherein said microorganisms are methane-utilizers belonging to the genera selected from the group consisting of: Methylosinus, Methylocystis, Methylomonas, Methylobacter, Methylococcus and Methylobacterium.

5. The process of claim 4 wherein said methane-utilizing microorganisms are species selected from the group consisting of: *Methylosinus trichosporium, Methylosinus sporium, Methylocystis parvus, Methylomonas methanica, Methylomonas albus, Methylomonas streptobacterium, Methylomonas agile, Methylomonas rubrum, Methylomonas rosaceus, Methylobacter chrooccum, Methylobacter bovis, Methylobacter capsulatus, Methylobacter vinelandii, Methyloccus capsulatus, Methylococcus minimus* and *Methylobacterium organophilum*.

6. The process of claim 5 wherein said methane-utilizing microorganisms are strains having the designations selected from the group consisting of: *Methylosinus trichosporium* OB3b (NRRL B-11,196); *Methylosinus sporium* 5 (NRRL B-11,197); *Methylocystis parvus* OBBP (NRRL B-11,198); *Methylomonas methanica* $S_1$ (NRRL B-11,199); *Methylomonas albus* BG8 (NRRL B-11,200); *Methylobacter capsulatus* Y (NRRL B-11,201); *Methylococcus capsulatus* (Texas) ATCC 19069; *Methylobacterium organophilum* sp. nov (ATCC 27,886); *Methylomonas sp.* AJ-3670 (FERM P-2400); *Methylococcus* 999 (NCIB Accession No. 11083); and *Methlomonas SM*3 (NCIB Accession No. 11084).

7. The process of claim 1 wherein said microorganisms are methano-utilizers belonging to the genera selected from the group consisting of: Methanomonas; Pseudomonas; Bacterium; Hyphomicrobium; Achromobacter; Protaminobacter; Vibro; Rhodopseudomonas; Bacillus; Brevibacterium; Candida; Hansenula; Pichia.

8. The process of claim 1 wherein said microorganisms are obligate methanol-utilizing methylotrophic microorganisms selected from the group consisting of: *Methanomonas methylovora* ATCC 21852; *Pseudomonas sp.* ATCC 21439; *Pseudomonas w*$_1$; *Bacterium C*$_2A_1$; *Bacterium 4B*6; *Hyphomicrobium sp.; Achromobacter sp.*;

9. The process of claim 1 wherein said microorganisms are facultative methanol-utilizing methylotrophic microorganisms selected from the group consisting of: *Pseudomonas sp.* ATCC 21439; *Pseudomonas AM*$_1$; Hyphomicrobium sp.; Protaminobacter ruber; Vibrio extroquens; Rhodopseudomonas acidophila; Pseudomonas MS ATCC 25262; *Achromobacter rufescens; Bacillus soraceus; Brevibacterium sp.; Pseudomonas M*$_{27}$; and *Pseudomonas C.*

10. The process of claim 7 wherein the carbon-containing compound is selected from the group consisting of methanol, ethanol, n-propanol, n-butanol, methylamine and methyl formate.

11. The process of any of claims 1, 2, 3, 4, 5, 6, 7, 8, 9 or 10 wherein said enzyme preparation is derived from a cell-free extract of said microbial cells and additionally contains endogenous or exogeneous NAD+.

12. The process of any of claims 1, 2, 3, 4, 5, 6, 7, 8, 9 or 10 wherein said enzyme preparation comprises:
(a) a dehydrogenase enzyme characterized as having a molecular weight of about 95,000±3,000 datlon as determined by Bio-gel column chromatography and two zinc atoms per molecule of protein and converting $C_3$-$C_6$ secondary alcohols to methyl ketones, under aerobic conditions, in the presence of nicotinamide adenine dinucleotide (NAD+) and
(b) nicotinamide adenine dinucleotide (NAD+).

13. A secondary alcohol dehydrogenase enzyme which converts $C_3$-$C_6$ secondary alcohols to the corresponding methyl ketones under aerobic conditions and further characterized as being derived from cells of a methylotrophic microorganism which has been previously grown under aerobic conditions in a nutrient medium containing a carbon containing compound which provides the carbon and energy source for growth of the cells of the microorganism and induces $C_3$-$C_6$ secondary alcohol dehydrogenase enzyme activity in said cells.

14. The enzyme of claim 13 wherein the enzyme is derived from microorganisms selected from the group consisting of bacteria, fungi and yeast grown under aerobic conditions in the presence of methyl radical donating compounds.

15. The enzyme of claim 14 wherein the methyl radical donating compound is selected from the group consisting of methane, methanol, ethanol, n-propanol, n-butanol, methylamine and methyl formate.

16. The enzyme of claim 13 wherein the enzyme is in the form of a soluble extract of the cells of said microorganism.

17. The enzyme of claim 13 wherein the enzyme is in substantially purified form.

18. The enzyme of claim 13 wherein the enzyme is further characterized as having a molecular weight of about 95,000±3,000 dalton as determined by Bio-gel column chromatography and two zinc atoms per molecule of protein.

19. The enzyme of claims 16, 17 or 18 which additionally includes nicotinamide adenine dinucleotide (NAD+).

20. A process for preparing a $C_3$-$C_6$ secondary alcohol dehydrogenase enzyme, comprising:
(a) cultivating, under aerobic conditions, an obligate or facultative methylotrophic microorganism in a nutrient medium containing a methyl radical donating compound in an amount sufficient to induce enzyme activity whereby microbial cells are obtained containing secondary alcohol dehydrogenase activity;
(b) recovering and disrupting said cells;
(c) removing the cellular debris and recovering the supernatant and isolating the enzyme containing the secondary alcohol dehydrogenase activity therefrom, said enzyme converting secondary alcohol to the corresponding methyl ketone.

21. A procee for converting C3-C6 secondary alcohols to the corresponding methyl ketones comprising:
oxidizing said alcohols under aerobic conditions in the presence of nicotinamide adenine dinucleotide (NAD+) and a cell-free enzyme preparation of C3-C6 secondary alcohol dehydrogenase and producing said methyl ketones in isolable amounts.

22. The process of claim 21 wherein said dehydrogenase enzyme is characterized as having a molecular weight of about 95,000±3,000 dalton as determined by Bio-gel column chromatography and two zinc atoms per molecule of protein.

23. The process of claims 21 or 22 wherein the enzyme is in a substantially purified form.

24. The process of claims 21 or 22 wherein the conversion is carried out at a temperature ranging from about 5° to about 55° C. and at a pH in the range from about 4 to about 9.

25. The process of claims 21 or 22 wherein the conversion is carried out in a continuous manner and the enzyme is immobilized.

26. Secondary alcohol dehydrogenase enzyme characterized as having a molecular weight of about 95,000±3,000 dalton as determined by Bio-gel column chromatography and two zinc atoms per molecule of protein.

27. The enzyme of claim 26 which additionally includes nicotinamide adenine dinucleotide (NAD+).

28. The enzyme of claim 26 wherein the enzyme is in substantially purified form.

29. The enzyme of claim 26 which has been immobilized.

* * * * *